US011904010B2

(12) United States Patent
Ma et al.

(10) Patent No.: US 11,904,010 B2
(45) Date of Patent: Feb. 20, 2024

(54) RECOMBINANT VIRUS CAPABLE OF STABLY EXPRESSING TARGET PROTEINS

(71) Applicant: BOEHRINGER INGELHEIM VETMEDICA (CHINA) CO., LTD., Jiangsu (CN)

(72) Inventors: Guanggang Ma, Shanghai (CN); Sen Yuan, Shanghai (CN)

(73) Assignee: BOEHRINGER INGELHEIM VETMEDICA (CHINA) CO., LTD.

( * ) Notice: Subject to any disclaimer, the term of this patent is extended or adjusted under 35 U.S.C. 154(b) by 475 days.

(21) Appl. No.: 17/046,210

(22) PCT Filed: Mar. 14, 2019

(86) PCT No.: PCT/CN2019/078057
§ 371 (c)(1),
(2) Date: Oct. 8, 2020

(87) PCT Pub. No.: WO2019/179345
PCT Pub. Date: Sep. 26, 2019

(65) Prior Publication Data
US 2021/0353734 A1 Nov. 18, 2021

(30) Foreign Application Priority Data
Mar. 19, 2018 (WO) ................ PCT/CN2018/079410

(51) Int. Cl.

| | |
|---|---|
| *A61K 39/12* | (2006.01) |
| *C12N 7/00* | (2006.01) |
| *A61K 39/00* | (2006.01) |

(52) U.S. Cl.
CPC ................ *A61K 39/12* (2013.01); *C12N 7/00* (2013.01); *A61K 2039/5256* (2013.01); *A61K 2039/552* (2013.01); *C12N 2770/32121* (2013.01); *C12N 2770/32122* (2013.01); *C12N 2770/32123* (2013.01); *C12N 2770/32134* (2013.01)

(58) Field of Classification Search
None
See application file for complete search history.

(56) References Cited

U.S. PATENT DOCUMENTS

2007/0065912 A1* 3/2007 Carson .................. C12N 15/67 435/348
2009/0264509 A1* 10/2009 Brough ................. A61K 39/12 435/320.1

(Continued)

FOREIGN PATENT DOCUMENTS

CN 101444622 A 6/2009
CN 107723281 A 2/2018

(Continued)

OTHER PUBLICATIONS

Rosas et al. (Journal of General Virology. 2007; 88: 748-757).*

(Continued)

*Primary Examiner* — Shanon A. Foley
(74) *Attorney, Agent, or Firm* — Duane Morris LLP; Thomas J. Kowalski; Deborah L. Lu

(57) ABSTRACT

Provided is a method to generate a recombinant virus that can stably express target proteins. The recombinant virus of the present invention is useful for producing an immunogenic composition or vaccine.

25 Claims, 6 Drawing Sheets

Specification includes a Sequence Listing.

(56) References Cited

U.S. PATENT DOCUMENTS

| | | | | |
|---|---|---|---|---|
| 2017/0143819 | A1* | 5/2017 | Audonnet | A61K 39/385 |
| 2019/0284577 | A1* | 9/2019 | Koukuntla | A61K 39/145 |
| 2021/0353734 | A1* | 11/2021 | Ma | A61K 39/12 |

FOREIGN PATENT DOCUMENTS

| | | |
|---|---|---|
| JP | 7-502403 A | 3/1995 |
| RU | 2546247 C2 | 4/2015 |
| WO | 93/11251 A1 | 6/1993 |
| WO | 0136651 A1 | 5/2001 |

OTHER PUBLICATIONS

Hong et al. (Biotechnology Letters. 2007; 29: 1677-1683).*
Zhang et al. (Research in Veterinary Science. 2011; 91: 90-94).*
Papagatsias et al. (Immunology Letters. 2008; 115: 117-125).*
Raul Andino, et al., Engineering Poliovirus as a Vaccine Vector for the Expression of Diverse Antigens, Science (Sep. 2, 1994) vol. 265, p. 1448-1451.
First Office Action dated Feb. 15, 2023 in co-pending Canadian Application No. 3,094,416.
Hui-Chen Guo, et al., Foot-and-mouth disease virus-like particles produced by a SUMO fusion protein system in *Escherichia coli* induce potent protective immune responses in guinea pigs, swine and cattle, Veterinary Research (Jul. 4, 2013) vol. 44, No. 1, p. 48.
L. Robinson, et al., Global Foot-and-Mouth Disease Research Update and Gap Analysis: 3—Vaccines, Transboundary and Emerging Diseases (Jun. 1, 2016) vol. 63 (Suppl. 1) p. 30-41.
Extended EP Search Report dated Dec. 8, 2021 in corresponding EP Application No. 19770578.3.
S. N. Beljelarskaya, Baculovirus Expression Systems for Recombinant Protein Production in Insect and Mammalian Cells, Molecular Biology (2011) vol. 45, No. 1, 142-159.
Qian, Ping, et al. Abstract: Construction of the Recombinant Pseudorabies Virus Expressing the GP2 Gene of Porcine Reproductive and Respiratory Syndrome Virus, Chinese Journal of Biochemistry and Molecular Biology (2003) vol. 19, No. 3, p. 391-395.
Russian Office Action dated Aug. 25, 2022 in co-pending Russian Patent Application No. 2020 133 457.
Abstract: S. Hamm, et al., Increasing Coding Capacity and Transgene Stability in Recombinant Vesicular Stomatitis Virus, AIDS Research and Human Retroviruses (2010) vol. 26, No. 10. p. 19.09.
Constance Klopfleisch, et al., Effect of foot and mouth disease virus capsid precursor protein and 3C protease expression on bovine herpesvirus 1 replication, Arch Virology (2010) 155:723-731.
Gorben P. Pijlman, et al., Stabilized baculovirus vector expressing a heterologous gene and GP64 from a single bicistronic transcript, Journal of Biotechnology (2006) vol. 123, p. 13-21.
John M. Thomas, et al., Sindbis Virus Vectors Designed to Express a Foreign Protein as a Cleavable Component of the Viral Structural Polyprotein, Journal of Virology (2003) vol. 77, No. 10, p. 5598-5606.
Japanese Office Action dated Jan. 26, 2023 issued in co-pending Japanese Application No. 2020-551267.
N.H.S. Histova, Immunobiological drugs for the prevention and treatment of infectious diseases and correction of dysbiocenoses (2007) p. 5; https://mkgtu.ru/sveden/files/Immunobiologicheskie_preparaty_dlya_profilaktiki_i_lecheniya_infekcionnyx_zabolevaniy(1).pdf.
A. McGregor, et al. Identification of Essential and Non-Essential Genes of the Guinea Pig Cytomegalovirus (GPCMV) Genome Via Transposome Mutagenesis of an Infectious BAC Clone, Virus Research (Feb. 20, 2004) vol. 101. No. 2, pp. 101-108.
International Search Report dated Apr. 30, 2019 in International Application No. PCT/CN2019/078057.

* cited by examiner

SEQUENCE LISTING

```
<160> NUMBER OF SEQ ID NOS: 15

<210> SEQ ID NO 1
<211> LENGTH: 2205
<212> TYPE: DNA
<213> ORGANISM: Foot-and-mouth disease virus

<400> SEQUENCE: 1
atgggagccg gacaatccag tccggctact gggtcacaga accaatcagg caacaccggg     60
agtatcatca acaattacta catgcagcag taccagaact ccatggacac ccaacttggt    120
gacaatgcta tcagcggagg ctccaacgag ggatccacag acacaacctc cacccacaca    180
accaacactc agaacaatga ctggttttca aagttggcca gctctgcctt cagcggtctt    240
ttcggcgccc tcctcgccga taagaaaacc gaggagacca ctcttctcga ggaccgcatc    300
ctcaccaccc gaaacggaca caccacctcg acaacccagt cgagtgttgg cataacgcac    360
gggtacgcaa cagctgagga tttttgtgaac gggccaaaca cctctggtct tgagaccaga    420
gttgtccagg cggaacggtt ctttaaaacc cacctgttcg actgggtcac cagtgatccg    480
ttcggacggt gctacttgtt ggagctcccg actgaccaca aaggtgtcta cggcagcctg    540
accgactcat acgcctacat gagaaacggt tgggatgttg aggtcaccgc tgtggggaat    600
cagttcaacg gaggctgcct actggtggcc atggtgcctg aactttgttc catcgagcgg    660
agagagctgt tccagcttac gctcttcccc caccagttca tcaaccccg gacgaacatg    720 acagcccaca tcaaggtgcc ctttgttggc gtcaaccgtt acgatcagta caaggtacac    780
aagccgtgga cccttgtggt tatggtcgta gccccactga ctgtcaacac cgaaggcgct    840
ccgcagatca aggtgtatgc caacatcgca cccaccaacg tgcacgtcgc gggtgagttc    900
ccttccaaag agggattt ccctgtggcc tgtagcgacg gttatggcgg cttggtgaca    960
actgacccaa agacggctga ccccgtttac ggcaaagtgt tcaaccccc ccgcaacatg    1020 ttgccggggc ggttcaccaa cctcctggac gtggctgagg cttgccccac gttttctgcac    1080 ttcgatggtg acgtaccgta tgtgaccact aagacggatt cggacagggt gctcgcacaa    1140
tttgacttgt ctttggcagc aaaacacatg tcaaacacct tccttgcagg tcttgcccag    1200
tactacacgc agtacagcgg caccgtcaac ctgcacttca tgttcacagg tcccactgac    1260
gcgaaagcgc gttacatgat tgcgtatgcc cctccgggca tggagccgcc caaaacacct    1320
gaggctgctg ctcactgcat tcacgcagag tgggacacgg gtctgaactc aaagtttacc    1380
```

| | |
|---|---|
| ttttccatcc cctacctctc ggcggctgat tacgcgtaca ccgcgtctga cgctgctgag | 1440 |
| accacaaatg ttcagggatg ggtctgctta tttcaaataa cacacgggaa agctgagggt | 1500 |
| gacgctcttg tcgtgctggc cagtgctggc aaagactttg agctgcgcct gcctgtggac | 1560 |
| gctcggcaac agaccacttc gacgggcgag tcggctgacc ccgtgactgc caccgttgag | 1620 |
| aattacggtg gcgagacaca ggtccagagg cgccaccaca cagacgtctc attcatattg | 1680 |
| gacagatttg tgaaagtcac accaaaagac tcaataaatg tattggacct gatgcagacc | 1740 |
| ccctcccaca ccctagtagg ggcgctcctc cgcactgcca cttactattt cgctgatcta | 1800 |
| gaggtggcag tgaaacacga gggggacctt acctgggtgc caaatggagc acctgaagca | 1860 |
| gccttggaca acaccaccaa cccaacggcg taccataagg cgccgcttac tcggcttgca | 1920 |
| ttgccctaca cggcaccaca ccgtgttttg gccaccgttt acaacgggaa ctgcaaatac | 1980 |
| gccgggggct cactgcccaa cgtgagaggc gatctccaag tgctggctca gaaggcagcg | 2040 |
| aggccgctgc ctacttcttt caactacggt gccatcaaag ccactcgggt gacagaactg | 2100 |
| ctgtaccgca tgaagagggc cgagacgtac tgtcctcggc ccctcttggc tgttcacccg | 2160 |
| agtgcggcca gacacaaaca gaaaatagtg gcgcctgtaa agcag | 2205 |

<210> SEQ ID NO 2
<211> LENGTH: 54
<212> TYPE: DNA
<213> ORGANISM: Foot-and-mouth disease virus

<400> SEQUENCE: 2

| | |
|---|---|
| tccttgaact ttgatctgct caagttggca ggggacgtgg agtccaaccc tggg | 54 |

<210> SEQ ID NO 3
<211> LENGTH: 642
<212> TYPE: DNA
<213> ORGANISM: Foot-and-mouth disease virus

<400> SEQUENCE: 3

| | |
|---|---|
| agtggtgccc ccccgaccga cttgcaaaag atggtcatgg gtaacaccaa gcccgttgag | 60 |
| ctcatactcg acgggaagac agtagccatc tgctgtgcta ctggagtatt tggcactgcc | 120 |
| tacctcgtgc ctcgtcatct tttcgctgag aagtacgaca agatcatgtt ggacggtaga | 180 |
| accatgacag acagtgacta cagagtgttt gagtttgaga ttaaagtaaa aggacaggac | 240 |
| atgctctcag acgctgcgct catggtgctg caccgtggga accgcgtgag agacatcacg | 300 |
| aaacactttc gtgacacagc aagaatgaag aaaggcaccc ccgtcgttgg tgtgatcaac | 360 |
| aacgctgacg tcgggagact gattttctca ggtgaggccc tcacctacaa ggacattgta | 420 |
| gtgtgcatgg atggagacac catgccgggc ctatttgcct acaaagccgc caccaaagct | 480 |
| ggctactgcg ggggagccgt ccttgctaag gatggagccg acacattcat cgttggcact | 540 |
| cactctgcag gtggcaatgg agttgggtac tgctcatgcg tatccagatc catgctccaa | 600 |
| aaaatgaagg cacacatcga ccctgaacca caccacgagt aa | 642 |

<210> SEQ ID NO 4
<211> LENGTH: 2985
<212> TYPE: DNA
<213> ORGANISM: Artificial Sequence
<220> FEATURE:
<223> OTHER INFORMATION: P1-2A-3C gene expression cassette

<400> SEQUENCE: 4

| | |
|---|---|
| atgggagccg gacaatccag tccggctact gggtcacaga accaatcagg caacaccggg | 60 |

```
agtatcatca acaattacta catgcagcag taccagaact ccatggacac ccaacttggt    120
gacaatgcta tcagcggagg ctccaacgag ggatccacag acacaacctc cacccacaca    180
accaacactc agaacaatga ctggttttca agttggcca gctctgcctt cagcggtctt     240
ttcggcgccc tcctcgccga taagaaaacc gaggagacca ctcttctcga ggaccgcatc    300
ctcaccaccc gaaacggaca caccacctcg acaacccagt cgagtgttgg cataacgcac    360
gggtacgcaa cagctgagga ttttgtgaac gggccaaaca cctctggtct tgagaccaga    420
gttgtccagg cggaacggtt ctttaaaacc cacctgttcg actgggtcac cagtgatccg    480
ttcggacggt gctacttgtt ggagctcccg actgaccaca aggtgtctca cggcagcctg    540
accgactcat acgcctacat gagaaacggt tgggatgttg aggtcaccgc tgtggggaat    600
cagttcaacg gaggctgcct actggtggcc atggtgcctg aactttgttc catcgagcgg    660
agagagctgt tccagcttac gctcttcccc caccagttca tcaaccccccg gacgaacatg    720 acagcccaca tcaaggtgcc ctttgttggc gtcaaccgtt acgatcagta caaggtacac    780
aagccgtgga cccttgtggt tatggtcgta gccccactga ctgtcaacac cgaaggcgct    840
ccgcagatca aggtgtatgc caacatcgca cccaccaacg tgcacgtcgc gggtgagttc    900
ccttccaaag agggattttt ccctgtggcc tgtagcgacg ttatggcgg cttggtgaca     960 actgacccaa agacggctga ccccgtttac ggcaaagtgt tcaaccccccc ccgcaacatg   1020 ttgccggggc ggttcaccaa cctcctggac gtggctgagg cttgccccac gtttctgcac   1080
ttcgatggtg acgtaccgta tgtgaccact aagacggatt cggacagggt gctcgcacaa   1140
tttgacttgt ctttggcagc aaaacacatg tcaaacacct tccttgcagg tcttgcccag   1200
tactacacgc agtacagcgg caccgtcaac ctgcacttca tgttcacagg tcccactgac   1260
gcgaaagcgc gttacatgat tgcgtatgcc cctccgggca tggagccgcc caaaacacct   1320
gaggctgctg ctcactgcat tcacgcagag tgggacacgg gtctgaactc aaagtttacc   1380
ttttccatcc cctacctctc ggcggctgat tacgcgtaca ccgcgtctga cgctgctgag   1440
accacaaatg ttcagggatg gtctgctta tttcaaataa cacacgggaa agctgagggt    1500
gacgctcttg tcgtgctggc cagtgctggc aaagactttg agctgcgcct gcctgtggac   1560
gctcggcaac agaccacttc gacgggcgag tcggctgacc ccgtgactgc caccgttgag   1620
aattacggtg gcgagacaca ggtccagagg cgccaccaca cagacgtctc attcatattg   1680
gacagatttg tgaaagtcac accaaaagac tcaataaatg tattggacct gatgcagacc   1740
ccctcccaca ccctagtagg ggcgctcctc cgcactgcca cttactattt cgctgatcta   1800
gaggtggcag tgaaacacga gggggacctt acctgggtgc caaatggagc acctgaagca   1860
gccttggaca acaccaccaa cccaacgccg taccataagg cgccgcttac tcggcttgca   1920
ttgccctaca cggcaccaca ccgtgttttg gccaccgttt acaacgggaa ctgcaaatac   1980
gccgggggct cactgcccaa cgtgagaggc gatctccaag tgctggctca gaaggcagcg   2040
aggccgctgc ctacttcttt caactacggt gccatcaaag ccactcgggt gacagaactg   2100
ctgtaccgca tgaagagggc cgagacgtac tgtcctcggc ccctcttggc tgttcacccg   2160
agtgcggcca gacacaaaca gaaaatagtg gcgcctgtaa agcagtcctt gaactttgat   2220
ctgctcaagt tggcagggga cgtggagtcc aaccctgggc ccggatctgg aggaccttac   2280
gagggaccgg tgaagaagcc tgtcgctttg aaagtgaaag ctaagaactt gatcgtcact   2340
gagagtggtg ccccccccgac cgacttgcaa aagatggtca tgggtaacac caagcccgtt   2400
```

```
gagctcatac tcgacgggaa gacagtagcc atctgctgtg ctactggagt atttggcact   2460
gcctacctcg tgcctcgtca tcttttcgct gagaagtacg acaagatcat gttggacggt   2520
agaaccatga cagacagtga ctacagagtg tttgagtttg agattaaagt aaaaggacag   2580
gacatgctct cagacgctgc gctcatggtg ctgcaccgtg ggaaccgcgt gagagacatc   2640
acgaaacact ttcgtgacac agcaagaatg aagaaaggca cccccgtcgt tggtgtgatc   2700
aacaacgctg acgtcgggag actgattttc tcaggtgagg ccctcaccta caaggacatt   2760
gtagtgtgca tggatggaga caccatgccg ggcctatttg cctacaaagc cgccaccaaa   2820
gctggctact gcgggggagc cgtccttgct aaggatggag ccgacacatt catcgttggc   2880
actcactctg caggtggcaa tggagttggg tactgctcat gcgtatccag atccatgctc   2940
caaaaaatga aggcacacat cgaccctgaa ccacaccacg agtaa                   2985
```

<210> SEQ ID NO 5
<211> LENGTH: 945
<212> TYPE: DNA
<213> ORGANISM: Equine herpesvirus 1

<400> SEQUENCE: 5

```
atggcgagtg ccgcctttga gattgacatc ctactgccca gtgacctatc tcccgctgac     60
ctgtcagctc ttcaaaaatg cgagggtaag cttgtgtttt tgaccgctct gcgtcgtcgc    120
gtgatgctct ccagcgtcac cctctcgtca tactatgtca acggcgcacc cccggacacg    180
ctatccctga tggcggcgtt tcgtaggcgt tttcccgcta taatacagcg cgtgctgccc    240
aacaaaatga tagccgccgc cctgggagtc gcaccgcttc ctcccggggc gttcatacag    300
aacacaggcc cgtttgacct gtgcaacggg gactctgtgt gcgcgctgcc tcccattttg    360
gacgtggagg acaagctgcg cctaggatct gtgggcgagg aaatactatt tccgctgacc    420
gttccactcg cgcaagcgcg cgaactcatc gcgcggctgg tagcgcgcgc ggtgcaggct    480
ctcaccccaa acgcccaggc ccagcgcgga gcggaggtga tgttttacaa cggacgaaag    540
tacaacgtga ccccggatct cagacaccga gacgccgtta acggcgtggc gcggtctctg    600
gtgctaaaca tgatttttgc catgaacgag ggatcgcttg tgctgctctc gctgatacca    660
aacctgctca ccctgggaac ccaggacgga tttgtgaacg ccataatcca gatgggaagc    720
gccacccgtg aggttggcca gctcgtccac cagcagcccg tgccccaacc gcaggacggc    780
gctcgccgct tttgtgtgta cgacgctctg atgtcatgga tcagcgttgc ctcgcgtctt    840
ggtgacgtgg tcggtgggaa acccttggtg cggatctgta cgttcgaggg ccaggctacg    900
atttcccgcg gcgagaaggc ccctgtcatt caaacgcttt tgtaa                    945
```

<210> SEQ ID NO 6
<211> LENGTH: 2256
<212> TYPE: DNA
<213> ORGANISM: Equine herpesvirus 1

<400> SEQUENCE: 6

```
atggagggca gcgtcgaatg gtttaacgga catgtttgtg ctaccagtat ttactctcta     60
tggacagatc cgcaccaccc agggcatctt caggcgctcg tctacatgct gtgtcggcgc    120
ggtagcgact acaccgcaga gttttgtcac gttcccgtct cgggcgaact cttgaaacgc    180
ggagctcgcg acgcatctct ggtaacaccg gcgcgcgttg ccagcgccgc gcagaccgcg    240
gctgtgcctg ggtgctggcc cctggctccc ctgggaaacg ccatgttgtg gaaatccgtc    300
tacggtggca taacggcggc gcttaagcgc gccgtgggaa gctttgcttt ctatcaaccc    360
```

```
ctggtgttag gaattaacac gcaaactgga cttttagtta ccctccgacc cgccgcgtct      420
gcgggtgaag gcggtggcga ccacgtctct ccgcgggcgg cgatcgtaaa tgtgtcggtg      480
gaggtagact tggacccagc gggcattgaa gcgagcgcgg ctagctccac aggatcgtct      540
ctcgccaggg ccagactctg cacgcttcga gatggatatt ttctctcaaa gcgggacatt      600
gccctagaag ttgagatcgc tacaaaggag gtttcatttt acagaaagta tgactctgtg      660
caacagcctg ccaacaagcg tcgcggcgac atggcagatt tgttcgtcgt gcacgaacga      720
acccttttgc taggggatg taaacgaatg ggagttaagg ttctattgcc gcgaacgttt      780
gactgtttag ttgccagctc ccagtcagtg tcgggtttag ctgccatggc gctgtacaaa      840
cagtggcacg ctactctatt ctctgtagag ctaccagata ctgttgtgca aatttttgct      900
tacctagggc cagaattaaa cccgtgtgga gaggaagtcg actattgttg ctttgttgga      960
tttcccggac tcccgaccct caaggctagt tcgagcacca cggaggctgt gcgcgatgca     1020
atggccgcct atagactgtc cgacgggctg tggccggctc taggtatgag cgcgtttcac     1080
tttttggctc catgggaccc ggaagacagg tggcccggtg aatcggaggc aaaacgggta     1140
gagggggcgg tacacaggct tcagcttgga accgaggatg attgggggc tgggcgggta     1200 tcatgcattt tagagtcgga cgctgtaatg caggggccgt ggttcgcaaa gtttgacttt     1260
tcggcgtttt tccccacgct gtacctgttg ctgtttcccg ccaatgagcg cttggctgag     1320
gtggttagat tgagggcacg tggccaacac cccacccttg agctcgcctt ggtatccttt     1380 tttgggggc tgcagcacat caaccccgta gcctataggt ccatcatagc cctatccaac     1440
ggaatcagta agcggctgga gcacgaagtc aatcagaggg gttttgccat ctgtacatat     1500
gtcaaagatg gcttttgggg gcagccgga aatctgccat cagactctgt atcctacgcc      1560
gacgcgctgg tttacgcaga ggagctaaga agcgccgctc agaaggcggc cctcggacac     1620
gtgtccgaga tggggtttc gctgccgag ggtgtccact tgaatttgcg gctggagggt     1680
ttgtttacag acgccatctc gtggtccacc cactgttact ggttgtacaa ccgcttcacc     1740
aagatggaag actttgtagg cttccccgcc aagagcgggg ccggcagagc cgcgaaggcg     1800
agcttgtctg ccttgctacc gctggtagcc gcggtatgcg actctagcga tatgagcacc     1860
ctccatcagt ctgtgcgggg ggcctgcgaa cagctggtag ccggcgcttt tgccgagcgc     1920
aacaacccgc agttttggag taccaggacg gggatcgagt cgtctacgct actcccccg      1980 gcagtttaca ggaacggcag cttgctcgac agagactgtg ggcagaggga aattgtgttg     2040
actcgcaaac acgactgtga atccccatcg cccgtaccct ggacgctctt cccaccaccc     2100
ttggttttgg ggcgcattga ctgtatggtc tatcttacgt ccattttcaa aacttatcta     2160
agcatgttaa acagagcaat atctgcctcg tgcgacgcgg atgaatctat gaatgtggac     2220
tttccaatct ctgattatgc attttttattt acctaa                              2256
```

<210> SEQ ID NO 7
<211> LENGTH: 225
<212> TYPE: DNA
<213> ORGANISM: Artificial Sequence
<220> FEATURE:
<223> OTHER INFORMATION: BGH polyA signal

<400> SEQUENCE: 7

```
gtcacctaaa tgctagagct cgctgatcag cctcgactgt gccttctagt tgccagccat       60
ctgttgtttg ccctccccc gtgccttcct tgaccctgga aggtgccact cccactgtcc      120
```

| | |
|---|---|
| tttcctaata aaatgaggaa attgcatcgc attgtctgag taggtgtcat tctattctgg | 180 |
| ggggtggggt ggggcaggac agcaaggggg aggattggga agaca | 225 |

<210> SEQ ID NO 8
<211> LENGTH: 4947
<212> TYPE: DNA
<213> ORGANISM: Artificial Sequence
<220> FEATURE:
<223> OTHER INFORMATION: CMV5-P12A3C2AORF43-BGH cassette

<400> SEQUENCE: 8

| | |
|---|---|
| ttattaatag taatcaatta cggggtcatt agttcatagc ccatatatgg agttccgcgt | 60 |
| tacataactt acggtaaatg gcccgcctgg ctgaccgccc aacgaccccc gcccattgac | 120 |
| gtcaataatg acgtatgttc ccatagtaac gccaataggg actttccatt gacgtcaatg | 180 |
| ggtggagtat ttacggtaaa ctgcccactt ggcagtacat caagtgtatc atatgccaag | 240 |
| tacgccccct attgacgtca atgacggtaa atggcccgcc tagcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc cgcgtggccg gccggatccg ccaccatggg agccggacaa | 660 |
| tccagtccgg ctactgggtc acagaaccaa tcaggcaaca ccgggagtat catcaacaat | 720 |
| tactacatgc agcagtacca gaactccatg acacccaac ttggtgacaa tgctatcagc | 780 |
| ggaggctcca acgagggatc cacagacaca acctccaccc acacaaccaa cactcagaac | 840 |
| aatgactggt ttcaaagtt ggccagctct gccttcagcg tcttttcgg cgccctcctc | 900 |
| gccgataaga aaaccgagga gaccactctt ctcgaggacc gcatcctcac cacccgaaac | 960 |
| ggacacacca cctcgacaac ccagtcgagt gttggcataa cgcacgggta cgcaacagct | 1020 |
| gaggattttg tgaacgggcc aaacacctct ggtcttgaga ccagagttgt ccaggcggaa | 1080 |
| cggttcttta aaacccacct gttcgactgg gtcaccagtg atccgttcgg acggtgctac | 1140 |
| ttgttggagc tcccgactga ccacaaaggt gtctacggca gcctgaccga ctcatacgcc | 1200 |
| tacatgagaa acggttggga tgttgaggtc accgctgtgg ggaatcagtt caacggaggc | 1260 |
| tgcctactgg tggccatggt gcctgaactt tgttccatcg agcggagaga gctgttccag | 1320 |
| cttacgctct tccccaccac gttcatcaac ccccggacga acatgacagc ccacatcaag | 1380 |
| gtgccctttg ttggcgtcaa ccgttacgat cagtacaagg tacacaagcc gtggaccctt | 1440 |
| gtggttatgg tcgtagcccc actgactgtc aacaccgaag gcgctccgca gatcaaggtg | 1500 |
| tatgccaaca tcgcacccac caacgtgcac gtcgcgggtg agttcccttc caaagagggg | 1560 |
| attttccctg tggcctgtag cgacggttat ggcggcttgg tgacaactga cccaaagacg | 1620 |
| gctgaccccg tttacggcaa agtgttcaac cccccccgca catgttgcc ggggcggttc | 1680 |
| accaacctcc tggacgtggc tgaggcttgc cccacgtttc tgcacttcga tggtgacgta | 1740 |
| ccgtatgtga ccactaagac ggattcggac aggtgctcg cacaatttga cttgtctttg | 1800 |
| gcagcaaaaa acatgtcaaa caccttcctt gcaggtcttg cccagtacta cacgcagtac | 1860 |
| agcggcaccg tcaacctgca cttcatgttc acaggtccca ctgacgcgaa agcgcgttac | 1920 |
| atgattgcgt atgcccctcc gggcatggag ccgcccaaaa cacctgaggc tgctgctcac | 1980 |

```
tgcattcacg cagagtggga cacgggtctg aactcaaagt ttaccttttc catcccctac    2040
ctctcggcgg ctgattacgc gtacaccgcg tctgacgctg ctgagaccac aaatgttcag    2100
ggatgggtct gcttatttca aataacacac gggaaagctg agggtgacgc tcttgtcgtg    2160
ctggccagtg ctggcaaaga ctttgagctg cgcctgcctg tggacgctcg gcaacagacc    2220
acttcgacgg gcgagtcggc tgaccccgtg actgccaccg ttgagaatta cggtggcgag    2280
acacaggtcc agaggcgcca ccacacagac gtctcattca tattggacag atttgtgaaa    2340
gtcacaccaa aagactcaat aaatgtattg gacctgatgc agaccccctc ccacacccta    2400 gtagggcgc tcctccgcac tgccacttac tatttcgctg atctagaggt ggcagtgaaa    2460
cacgaggggg accttacctg ggtgccaaat ggagcacctg aagcagcctt ggacaacacc    2520
accaacccaa cggcgtacca taaggcgccg cttactcggc ttgcattgcc ctacacggca    2580
ccacaccgtg ttttggccac cgtttacaac gggaactgca aatacgccgg gggctcactg    2640
cccaacgtga gaggcgatct ccaagtgctg gctcagaagg cagcgaggcc gctgcctact    2700
tctttcaact acggtgccat caaagccact cgggtgacag aactgctgta ccgcatgaag    2760
agggccgaga cgtactgtcc tcggcccctc ttggctgttc acccgagtgc ggccagacac    2820
aaacagaaaa tagtggcgcc tgtaaagcag tccttgaact ttgatctgct caagttggca    2880
ggggacgtgg agtccaaccc tgggcccgga tctggaggac cttacgaggg accggtgaag    2940
aagcctgtcg ctttgaaagt gaaagctaag aacttgatcg tcactgagag tggtgccccc    3000
ccgaccgact tgcaaaagat ggtcatgggt aacaccaagc ccgttgagct catactcgac    3060
gggaagacag tagccatctg ctgtgctact ggagtatttg gcactgccta cctcgtgcct    3120
cgtcatcttt tcgctgagaa gtacgacaag atcatgttgg acggtagaac catgacagac    3180
agtgactaca gagtgtttga gtttgagatt aaagtaaaag acaggacat gctctcagac    3240 gctgcgctca tggtgctgca ccgtgggaac cgcgtgagag acatcacgaa acactttcgt    3300
gacacagcaa gaatgaagaa aggcaccccc gtcgttggtg tgatcaacaa cgctgacgtc    3360
gggagactga ttttctcagg tgaggccctc acctacaagg acattgtagt gtgcatggat    3420
ggagacacca tgccgggcct atttgcctac aaagccgcca ccaaagctgg ctactgcggg    3480
ggagccgtcc ttgctaagga tggagccgac acattcatcg ttggcactca ctctgcaggt    3540
ggcaatggag ttgggtactg ctcatgcgta tccagatcca tgctccaaaa aatgaaggca    3600
cacatcgacc ctgaaccaca ccacgagggg ttgatcgttg acaccagaga tgtggaagag    3660
cgcgtgcacg tcatgcgcaa gaccaagggt acctccttga actttgatct cctcaagttg    3720 gcagggacg tagagtccaa cccagggcct atggcgagtg ccgcctttga gattgacatc    3780
ctactgccca gtgacctatc tcccgctgac ctgtcagctc ttcaaaaatg cgagggtaag    3840
cttgtgtttt tgaccgctct gcgtcgtcgc gtgatgctct ccagcgtcac cctctcgtca    3900
tactatgtca acggcgcacc cccggacacg ctatccctga tggcggcgtt tcgtaggcgt    3960
tttcccgcta aatacagcg cgtgctgccc aacaaaatga tagccgccgc cctgggagtc    4020
gcaccgcttc ctcccggggc gttcatacag aacacaggcc cgtttgacct gtgcaacggg    4080
gactctgtgt gcgcgctgcc tcccattttg acgtggagac acaagctgcg cctaggatct    4140
gtgggcgagg aaatactatt tccgctgacc gttccactcg cgcaagcgcg cgaactcatc    4200
gcgcggctgg tagcgcgcgc ggtgcaggct ctcaccccaa acgcccaggc ccagcgcgga    4260
gcggaggtga tgttttacaa cggacgaaag tacaacgtga ccccggatct cagacaccga    4320
```

-continued

| | |
|---|---|
| gacgccgtta acggcgtggc gcggtctctg gtgctaaaca tgattttttgc catgaacgag | 4380 |
| ggatcgcttg tgctgctctc gctgatacca aacctgctca ccctgggaac ccaggacgga | 4440 |
| tttgtgaacg ccataatcca gatgggaagc gccacccgtg aggttggcca gctcgtccac | 4500 |
| cagcagcccg tgccccaacc gcaggacggc gctcgccgct tttgtgtgta cgacgctctg | 4560 |
| atgtcatgga tcagcgttgc ctcgcgtctt ggtgacgtgg tcggtgggaa acccttggtg | 4620 |
| cggatctgta cgttcgaggg ccaggctacg atttcccgcg gcgagaaggc ccctgtcatt | 4680 |
| caaacgcttt tgtaatctag atagagggcc ctattctata gtgtcaccta atgctagag | 4740 |
| ctcgctgatc agcctcgact gtgccttcta gttgccagcc atctgttgtt tgcccctccc | 4800 |
| ccgtgccttc cttgaccctg gaaggtgcca ctcccactgt cctttcctaa taaaatgagg | 4860 |
| aaattgcatc gcattgtctg agtaggtgtc attctattct ggggggtggg gtggggcagg | 4920 |
| acagcaaggg ggaggattgg gaagaca | 4947 |

<210> SEQ ID NO 9
<211> LENGTH: 6258
<212> TYPE: DNA
<213> ORGANISM: Artificial Sequence
<220> FEATURE:
<223> OTHER INFORMATION: CMV5-P12A3C2AORF54-BGH cassette

<400> SEQUENCE: 9

| | |
|---|---|
| ttattaatag taatcaatta cggggtcatt agttcatagc ccatatatgg agttccgcgt | 60 |
| tacataactt acggtaaatg gcccgcctgg ctgaccgccc aacgacccccc gcccattgac | 120 |
| gtcaataatg acgtatgttc ccatagtaac gccaataggg actttccatt gacgtcaatg | 180 |
| ggtggagtat ttacggtaaa ctgcccactt ggcagtacat caagtgtatc atatgccaag | 240 |
| tacgcccccct attgacgtca atgacggtaa atggcccgcc tagcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |
| aaaatgtcgt aacaactccg ccccattgac gcaaatgggc ggtaggcgtg tacggtggga | 600 |
| ggtctatata agcagagctc cgcgtggccg gccggatccg ccaccatggg agccggacaa | 660 |
| tccagtccgg ctactgggtc acagaaccaa tcaggcaaca ccgggagtat catcaacaat | 720 |
| tactacatgc agcagtacca gaactccatg gacacccaac ttggtgacaa tgctatcagc | 780 |
| ggaggctcca acgagggatc cacagacaca acctccaccc acacaaccaa cactcagaac | 840 |
| aatgactggt tttcaaagtt ggccagctct gccttcagcg gtctttttcgg cgccctcctc | 900 |
| gccgataaga aaaccgagga ccactctctt ctcgaggacc gcatcctcac cacccgaaac | 960 |
| ggacacacca cctcgacaac ccagtcgagt gttggcataa cgcacgggta cgcaacagct | 1020 |
| gaggattttg tgaacgggcc aaacacctct ggtcttgaga ccagagttgt ccaggcggaa | 1080 |
| cggttctttta aacccacct gttcgactgg gtcaccagtg atccgttcgg acggtgctac | 1140 |
| ttgttggagc tcccgactga ccacaaaggt gtctacggca gcctgaccga ctcatacgcc | 1200 |
| tacatgagaa acggttggga tgttgaggtc accgctgtgg ggaatcagtt caacggaggc | 1260 |
| tgcctactgg tggccatggt gcctgaactt tgttccatcg agcggagaga gctgttccag | 1320 |
| cttacgctct tcccccacca gttcatcaac ccccggacga catgacagc ccacatcaag | 1380 |
| gtgccctttg ttggcgtcaa ccgttacgat cagtacaagg tacacaagcc gtggacccctt | 1440 |

```
gtggttatgg tcgtagcccc actgactgtc aacaccgaag gcgctccgca gatcaaggtg    1500
tatgccaaca tcgcacccac caacgtgcac gtcgcgggtg agttcccttc caaagagggg    1560
attttccctg tggcctgtag cgacggttat ggcggcttgg tgacaactga cccaaagacg    1620
gctgaccccg tttacggcaa agtgttcaac cccccccgca acatgttgcc ggggcggttc    1680
accaacctcc tggacgtggc tgaggcttgc cccacgtttc tgcacttcga tggtgacgta    1740
ccgtatgtga ccactaagac ggattcggac agggtgctcg cacaatttga cttgtctttg    1800
gcagcaaaac acatgtcaaa caccttcctt gcaggtcttg cccagtacta cacgcagtac    1860
agcggcaccg tcaacctgca cttcatgttc acaggtccca ctgacgcgaa agcgcgttac    1920
atgattgcgt atgcccctcc gggcatggag ccgcccaaaa cacctgaggc tgctgctcac    1980
tgcattcacg cagagtggga cacgggtctg aactcaaagt ttaccttttc catccsctac    2040
ctctcggcgg ctgattacgc gtacaccgcg tctgacgctg ctgagaccac aaatgttcag    2100
ggatgggtct gcttatttca aataacacac gggaaagctg agggtgacgc tcttgtcgtg    2160
ctggccagtg ctggcaaaga cttttgagctg cgcctgcctg tggacgctcg gcaacagacc    2220
acttcgacgg gcgagtcggc tgaccccgtg actgccaccg ttgagaatta cggtggcgag    2280
acacaggtcc agaggcgcca ccacacagac gtctcattca tattggacag atttgtgaaa    2340
gtcacaccaa aagactcaat aaatgtattg gacctgatgc agaccccctc ccacacccta    2400 gtagggcgc tcctccgcac tgccacttac tatttcgctg atctagaggt ggcagtgaaa    2460
cacgaggggg accttacctg ggtgccaaat ggagcacctg aagcagcctt ggacaacacc    2520
accaacccaa cggcgtacca taaggcgccg cttactcggc ttgcattgcc ctacacggca    2580
ccacaccgtg ttttggccac cgtttacaac gggaactgca aatacgccgg gggctcactg    2640
cccaacgtga gaggcgatct ccaagtgctg gctcagaagg cagcgaggcc gctgcctact    2700
tctttcaact acggtgccat caaagccact cgggtgacag aactgctgta ccgcatgaag    2760
agggccgaga cgtactgtcc tcggcccctc ttggctgttc acccgagtgc ggccagacac    2820
aaacagaaaa tagtggcgcc tgtaaagcag tccttgaact ttgatctgct caagttggca    2880
ggggacgtgg agtccaaccc tgggcccgga tctggaggac cttacgaggg accggtgaag    2940
aagcctgtcg ctttgaaagt gaaagctaag aacttgatcg tcactgagag tggtgccccc    3000
ccgaccgact tgcaaaagat ggtcatgggt aacaccaagc ccgttgagct catactcgac    3060
gggaagacag tagccatctg ctgtgctact ggagtatttg gcactgccta cctcgtgcct    3120
cgtcatcttt tcgctgagaa gtacgacaag atcatgttgg acggtagaac catgacagac    3180
agtgactaca gagtgtttga gtttgagatt aaagtaaaag acaggacat gctctcagac    3240 gctgcgctca tggtgctgca ccgtgggaac cgcgtgagac acatcacgaa acactttcgt    3300
gacacagcaa gaatgaagaa aggcacccccc gtcgttggtg tgatcaacaa cgctgacgtc    3360
gggagactga ttttctcagg tgaggccctc acctacaagg acattgtagt gtgcatggat    3420
ggagacacca tgccgggcct atttgcctac aaagccgcca ccaaagctgg ctactgcggg    3480
ggagccgtcc ttgctaagga tggagccgac acattcatcg ttggcactca ctctgcaggt    3540
ggcaatggag ttgggtactg ctcatgcgta tccagatcca tgctccaaaa aatgaaggca    3600
cacatcgacc ctgaaccaca ccacgagggg ttgatcgttg acaccagaga tgtggaagag    3660
cgcgtgcacg tcatgcgcaa gaccaagggt acctccttga actttgatct cctcaagttg    3720
gcaggggacg tagagtccaa cccagggcct atggagggca gcgtcgaatg gtttaacgga    3780
```

```
catgtttgtg ctaccagtat ttactctcta tggacagatc cgcaccaccc agggcatctt    3840
caggcgctcg tctacatgct gtgtcggcgc ggtagcgact acaccgcaga gttttgtcac    3900
gttcccgtct cgggcgaact cttgaaacgc ggagctcgcg acgcatctct ggtaacaccg    3960
gcgcgcgttg ccagcgccgc gcagaccgcg gctgtgcctg ggtgctggcc cctggctccc    4020
ctgggaaacg ccatgttgtg gaaatccgtc tacggtggca taacggcggc gcttaagcgc    4080
gccgtgggaa gctttgcttt ctatcaaccc ctggtgttag gaattaacac gcaaactgga    4140
cttttagtta ccctccgacc cgccgcgtct gcgggtgaag gcggtggcga ccacgtctct    4200
ccgcgggcgg cgatcgtaaa tgtgtcggtg gaggtagact tggacccagc gggcattgaa    4260
gcgagcgcgg ctagctccac aggatcgtct ctcgccaggg ccagactctg cacgcttcga    4320
gatggatatt ttctctcaaa gcgggacatt gccctagaag ttgagatcgc tacaaaggag    4380
gtttcatttt acagaaagta tgactctgtg caacagcctg ccaacaagcg tcgcggcgac    4440
atggcagatt tgttcgtcgt gcacgaacga acccttttgc taggggatg taaacgaatg    4500 ggagttaagg ttctattgcc gcgaacgttt gactgtttag ttgccagctc ccagtcagtg    4560
tcgggtttag ctgccatggc gctgtacaaa cagtggcacg ctactctatt ctctgtagag    4620
ctaccagata ctgttgtgca aattttgct tacctagggc cagaattaaa cccgtgtgga    4680
gaggaagtcg actattgttg ctttgttgga tttcccggac tcccgaccct caaggctagt    4740
tcgagcacca cggaggctgt gcgcgatgca atggccgcct atagactgtc cgacgggctg    4800
tggccggctc taggtatgag cgcgtttcac ttttggctc catgggaccc ggaagacagg    4860
tggcccggtg aatcggaggc aaaacgggta gagggggcgg tacacaggct tcagcttgga    4920
accgaggatg attgggggc tgggcgggta tcatgcattt tagagtcgga cgctgtaatg    4980
caggggccgt ggttcgcaaa gtttgacttt tcggcgtttt tccccacgct gtacctgttg    5040
ctgtttcccg ccaatgagcg cttggctgag gtggttagat tgagggcacg tggccaacac    5100 cccacccta agctcgcctt ggtatccttt tttgggggc tgcagcacat caaccccgta    5160
gcctataggt ccatcatagc cctatccaac ggaatcagta agcggctgga gcacgaagtc    5220
aatcagaggg gttttgccat ctgtacatat gtcaaagatg gcttttgggg ggcagccgga    5280
aatctgccat cagactctgt atcctacgcc gacgcgctgg tttacgcaga ggagctaaga    5340
agcgccgctc agaaggcggc cctcggacac gtgtccgaga tggggttttc gctgccggag    5400
ggtgtccact tgaatttgcg gctggagggt ttgtttacag acgccatctc gtggtccacc    5460
cactgttact ggttgtacaa ccgcttcacc aagatggaag actttgtagg cttccccgcc    5520
aagagcgggg ccggcagagc cgcgaaggcg agcttgtctg ccttgctacc gctggtagcc    5580
gcggtatgcg actctagcga tatgagcacc ctccatcagt ctgtgcgggg ggcctgcgaa    5640
cagctggtag ccggcgcttt tgccgagcgc aacaacccgc agttttggag taccaggacg    5700
gggatcgagt cgtctacgct actccccccg gcagtttaca ggaacggcag cttgctcgac    5760
agagactgtg ggcagaggga aattgtgttg actcgcaaac acgactgtga atccccatcg    5820
cccgtaccct ggacgctctt cccaccaccc ttggttttgg ggcgcattga ctgtatggtc    5880
tatcttacgt ccattttcaa aacttatcta agcatgttaa acagagcaat atctgcctcg    5940
tgcgacgcgg atgaatctat gaatgtggac tttccaatct ctgattatgc attttattt    6000 acctaatcta gatagagggc cctattctat agtgtcacct aaatgctaga gctcgctgat    6060
cagcctcgac tgtgccttct agttgccagc catctgttgt ttgcccctcc cccgtgcctt    6120
ccttgaccct ggaaggtgcc actcccactg tcctttccta ataaaatgag gaaattgcat    6180
```
cgcattgtct gagtaggtgt cattctattc tgggggggtgg ggtggggcag gacagcaagg    6240
gggaggattg ggaagaca                                                   6258

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
taacaccatg gcaggcctgt tg                                              22

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
gagcgattcg cacctcatct cc                                              22

<210> SEQ ID NO 12
<211> LENGTH: 37
<212> TYPE: DNA
<213> ORGANISM: Artificial Sequence
<220> FEATURE:
<223> OTHER INFORMATION: nucleotide sequence with one nucltide deletion

<400> SEQUENCE: 12
caaagtgttc aaccccccc gcaacatgtt gccgggg                               37

<210> SEQ ID NO 13
<211> LENGTH: 38
<212> TYPE: DNA
<213> ORGANISM: Artificial Sequence
<220> FEATURE:
<223> OTHER INFORMATION: nucleotide sequence without mutation

<400> SEQUENCE: 13
caaagtgttc aaccccccc cgcaacatgt tgccgggg                              38

<210> SEQ ID NO 14
<211> LENGTH: 38
<212> TYPE: DNA
<213> ORGANISM: Artificial Sequence
<220> FEATURE:
<223> OTHER INFORMATION: nucleotide sequence without mutation

<400> SEQUENCE: 14
caaagtgttc aaccccccc cgcaacatgt tgccgggg                              38

<210> SEQ ID NO 15
<211> LENGTH: 38
<212> TYPE: DNA
<213> ORGANISM: Artificial Sequence
<220> FEATURE:
<223> OTHER INFORMATION: nucleotide sequence without mutation

<400> SEQUENCE: 15
caaagtgttc aaccccccc cgcaacatgt tgccgggg                              38

RECOMBINANT VIRUS CAPABLE OF STABLY EXPRESSING TARGET PROTEINS

CROSS-REFERENCE TO RELATED APPLICATIONS

This application is a § 371 U.S. National Phase of international patent application Ser. No. PCT/CN2019/078057 filed Mar. 14, 2019, which published as PCT Publication No. WO 2019/1791345 on Sep. 26, 2019, which claims benefit of Chinese patent application Ser. No. PCT/CN2018/079410 filed Mar. 19, 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to the field of molecular biology, and especially to a recombinant virus that can stably express target proteins and the use thereof.

BACKGROUND OF THE INVENTION

Foot-and-mouth disease virus (FMDV) is a ribonucleic acid (RNA) virus belonging to the Aphthovirus genus of the Picornaviridae family (Cooper et al., Intervirology, 1978, 10, 165-180). As a naked icosahedral virus of about 25 nm in diameter, FMDV contains a single-stranded RNA molecule consisting of about 8500 nucleotides, with a positive polarity. This RNA molecule comprises a single open reading frame (ORF), encoding a single polyprotein containing, inter alia, the capsid precursor also known as protein P1. Protein P1 is myristylated at its amino-terminal end. During the maturation process, protein P1 is cleaved by protease 3C into three proteins known as VP0, VP1 and VP3 (Belsham G. J., Progress in Biophysics and Molecular Biology, 1993, 60, 241-261). In the virion, protein VP0 is then cleaved into two proteins, VP4 and VP2. The mechanism for the conversion of proteins VP0 into VP4 and VP2, and for the formation of mature virions is not known. Proteins VP1, VP2 and VP3 have a molecular weight of about 26,000 Da, while protein VP4 is smaller at about 8,000 Da.

In FMD-epidemic areas, vaccination is an effective and the major means to control the disease. Current commercial vaccines against FMDV mainly are whole inactivated FMDV vaccines. Production of such vaccines requires propagation of large volume of virulent FMDV in high-containment facility, which is expensive to maintain and has potential risk of releasing live FMDV. In addition, some field strains are difficult to be adapted to suspension BHK cells and reach high titer. Another issue of the whole inactivated vaccines is that it sometimes cannot effectively stimulate immune response, especially in pigs, and thus it needs regular booster injections.

One of novel FMD vaccines is a virus-like particles (VLPs)-based vaccine. Derived from the precursor protein P1-2A, VLPs contain the entire repertoire of immunogenic sites present on intact virus, and are as immunogenic as virions in animals. VLPs are lacking of nucleic acid and are not infectious, therefore, VLP-based vaccines have high safety profile in respect of production and use in animals. FMDV VLPs can be expressed using different expression systems and vectors, and can be delivered as subunit vaccines (Luis L. Rodriguez and Marvin J. Grubman, Foot and mouth disease virus vaccines, Vaccine 27 (2009) D90-D94). Despite the safety and easy preparation, the VLP-based subunit vaccines sometimes cannot successfully induce long lasting immunity against disease. Live vaccines can confer immunity in one or two doses, whereas the VLP-based subunit vaccines might need to be administered repeatedly over specified periods of time.

VLP-based live vectored vaccines are expected as a promising vaccine candidate for the control of FMDV. To develop FMDV VLP-based live vectored vaccines, a recombinant virus containing the VLP-encoding gene should be constructed. VLP-encoding gene should be composed of P1-2A precursor gene and 3C protease gene, so that VLP could be expressed and assembled automatically during the replication of the recombinant virus. Unfortunately, it was found that P1-2A genes cannot be stably maintained during continuous passages of the recombinant viruses for example adenovirus, which therefore will negatively affect the VLP yield and the vaccine efficacy. (L. Robinson, T. J. D. Knight-Jones, B. Charleston. Global Foot-and-Mouth Disease Research Update and Gap Analysis: 3—Vaccines. Transboundary and Emerging Diseases (2016) P30-41).

There is a need to develop a VLP-encoding gene-containing recombinant virus which can allow the VLP-encoding gene to be stably maintained in the recombinant virus during its continuous passages in vitro.

SUMMARY OF THE INVENTION

The solution to the above described technical problem is achieved by the description and the embodiments characterized in the claims and the invention in its different aspects is implemented according to the claims.

Generally, the present invention provides a recombinant virus and the related method for increasing the expression stability of a target gene.

In the above-mentioned recombinant virus, the target gene is designed to be functionally linked to an essential gene of the recombinant virus and located upstream of the essential gene, so that the target gene and the essential gene can be co-expressed. For example, the target gene can be inserted to the upstream of an essential gene of the recombinant virus within the same ORF, as such the target gene will be stably co-expressed with the essential gene so long as the recombinant virus could replicate. A recombinant virus with loss of target gene expression or any out-of-frame mutations in the target gene will not be able to replicate. In one embodiment, the recombinant virus is derived from herpesviridae, in particular Equid Alphaherpesvirus 1 (EHV-1). In one embodiment, the target gene comprises the P1 gene, 2A gene and 3C gene of FMDV. Within the context of the present description, the terms "target gene" and "the first polynucleotide" are interchangeable, and the terms "essential gene" and "the second polynucleotide" are interchangeable.

By using above-mentioned recombinant virus, the target gene can be stably expressed by the recombinant virus containing the same.

The present invention also provides a host cell comprising the recombinant virus of the present invention, and the preparation method thereof.

The present invention also provides an immunogenic composition, a pharmaceutical composition, or vaccine composition, comprising the recombinant virus of the present invention and/or the polypeptide of interest expressed by the recombinant virus of the present invention, and the preparation method thereof. The present invention also provides use of the recombinant virus of the present invention in preparation of an immunogenic/pharmaceutical/vaccine composition.

The present invention also provides a method for the treatment and/or prophylaxis of clinical signs caused by a virus in an animal by administering to the animal the recombinant virus of the present invention or the immunogenic/pharmaceutical/vaccine composition of the present invention.

The present invention further concerns a method for immunizing an animal such as a food producing animal including swine comprising administering to such an animal the recombinant virus of the present invention or the immunogenic/pharmaceutical/vaccine composition of the present invention.

DETAILED DESCRIPTION OF THE INVENTION

The present invention concerns a recombinant virus, comprising an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or a functional fragment thereof that is active in the recombinant virus.

The present invention also concerns a method for preparing a recombinant virus, comprising constructing an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or functional fragment thereof that is active in the recombinant virus.

The present invention further concerns a method for increasing the expression stability of a polypeptide of interest within a recombinant virus, comprising constructing an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or functional fragment thereof that is active in the recombinant virus.

The recombinant virus of the present invention is constructed based on a new idea of co-expressing of the target genes with an essential gene of the recombinant virus. It is expected that the co-expression of the target genes and the essential gene of the recombinant virus will be of benefit to the stable expression of the target proteins. The replication of the recombinant virus will be dependent on the expression of the target genes, which in turn makes the expression of target genes stable. If the recombinant virus loses the expression of target gene or has any out-of-frame mutations in the target gene, the downstream essential gene will not be functionally expressed either, and as a result, the recombinant virus will not be able to replicate. That is, by functionally combined together, the target gene will be stably expressed under a replication selection pressure.

The co-expression of the target genes and the essential gene of the recombinant virus can be achieved by allowing the target gene to be functionally linked to the essential gene. In an exemplary embodiment, the target gene and the essential gene can be designed to locate within the same ORF. Thus, in one embodiment, the first polynucleotide and the second polynucleotide of the recombinant virus of the present invention are within the same ORF.

There are two exemplary options to achieve the functional linking of the target gene to the essential gene. The first option is to delete or silence an endogenous essential gene of the recombinant virus (i.e. an essential gene naturally occurring in the genome of the recombinant virus), and insert a same essential gene which is exogenously introduced downstream of the target gene, so that the target gene is functionally linked to the essential gene. Thus, in one embodiment, the second polynucleotide is exogenous, and the endogenous essential gene of the recombinant virus has been silenced. The second option is to insert the target gene upstream of the endogenous essential gene of the virus, so that the target gene is functionally linked to the essential gene. Thus, in one embodiment, the second polynucleotide is the endogenous essential gene of the recombinant virus.

In one embodiment, the second polynucleotide is the endogenous essential gene of the recombinant virus. In another embodiment, the second polynucleotide is exogenous, and the endogenous essential gene of the recombinant virus has been silenced.

In one embodiment, the first polynucleotide encodes an antigenic polypeptide or a therapeutic polypeptide. The antigenic polypeptide can be selected from for example a group consisting of a FMDV antigen, a PRRSV antigen, a DEV antigen, and a PRV antigen, preferably a FMDV antigen. In one embodiment, the first polynucleotide comprises the P1 gene, 2A gene and 3C gene of FMDV. In one embodiment, the nucleotide sequence of P1 gene is shown by SEQ ID NO: 1. In one embodiment, the nucleotide sequence of 2A gene is shown by SEQ ID NO: 2. In one embodiment, the nucleotide sequence of 3C gene is shown by SEQ ID NO: 3. In one embodiment, the nucleotide sequence of the P1-2A-3C gene cassette is shown by SEQ ID NO: 4.

In one embodiment, the second polynucleotide is an essential gene of the recombinant virus or a functional fragment thereof. The essential genes are those genes of an organism that are thought to be critical for its replication. As for a virus, the essential genes include, but not limited to, those genes encoding capsid protein, DNA helicase, DNA replicase, etc. In one embodiment, the essential gene encodes a protein selected from for example the group consisting of a capsid protein, a DNA replication related protein, a DNA helicase, a DNA replicase, a receptor binding protein, and an Egress-related protein. In one embodiment, the essential gene is from the genome of EHV-1. In one embodiment, the essential gene is EHV-1 ORF43 gene or EHV-1 ORF54 gene. In one embodiment, the nucleotide sequence of ORF43 gene is shown by SEQ ID NO: 5. In one embodiment, the nucleotide sequence of ORF54 gene is shown by SEQ ID NO: 6.

In one embodiment, the first polynucleotide is linked to the second polynucleotide via a linker. In one embodiment, the linker can be a flexible linker such as (GGGGS)n linker, or a 2A gene, preferably a 2A gene. In one embodiment, the first polynucleotide is directly linked to the second polynucleotide. In one embodiment, the expression cassette comprises a construct shown by a structure of "the first polynucleotide-linker-the second polynucleotide".

In one embodiment, the recombinant virus is derived from the virus selected from for example herpesviridae such as Equid Alphaherpesvirus 1 (EHV-1), Equid Alphaherpesvirus 4 (EHV-4) and Bovine Alphaherpesvirus 1 (Bovine Herpesvirus 1, BHV-1). In one embodiment, the recombinant virus is derived from the virus selected from a member of the family Herpesviridae, preferably of the genus Alphaherpesvirinae, more preferably of the subgenus Varicellovirus, most preferably said recombinant virus is derived from Equid Alphaherpesvirus 1 (EHV-1).

In one embodiment, the recombinant virus is derived from EHV-1, and the first polynucleotide comprises the P1 gene, 2A gene and 3C gene of FMDV. In one embodiment, the nucleotide sequence of P1 gene is shown by SEQ ID NO: 1. In one embodiment, the nucleotide sequence of 2A gene is shown by SEQ ID NO: 2. In one embodiment, the nucleotide sequence of 3C gene is shown by SEQ ID NO: 3. In one embodiment, the nucleotide sequence of the P1-2A-3C gene cassette is shown by SEQ ID NO: 4. In one embodiment, the recombinant virus is derived from EHV-1, and the essential gene is EHV-1 ORF43 gene or EHV-1 ORF54 gene. In one embodiment, the nucleotide sequence of ORF43 gene is shown by SEQ ID NO: 5. In one embodiment, the nucleotide sequence of ORF54 gene is shown by SEQ ID NO: 6. In one embodiment, the recombinant virus is derived from EHV-1, the essential gene is EHV-1 ORF43 gene or EHV-1 ORF54 gene, and the first polynucleotide comprises the P1 gene, 2A gene and 3C gene of FMDV.

In one embodiment, the expression cassette further comprises for example regulatory elements, such as a promoter, terminator, etc. In one embodiment, the promoter is a CMV promoter. In one embodiment, the terminator is a polyA (polyadenylation) signal, preferably a BGH (Bovine Growth Hormone) polyA signal. In one embodiment, the nucleotide sequence of BGH polyA signal is shown by SEQ ID NO: 7.

In one embodiment, the expression cassette comprises a construct shown by a structure of "promoter-the first polynucleotide-the second polynucleotide-terminator". In one embodiment, the expression cassette comprises a construct shown by a structure of "promoter-the first polynucleotide-linker-the second polynucleotide-terminator". In one embodiment, the promoter is CMV promoter, preferably CMV5 promoter. In one embodiment, the first polynucleotide is the target gene, and it comprises or consists of the P1 gene, 2A gene and 3C gene of FMDV. In one embodiment, the second polynucleotide is the essential gene, and it is EHV-1 ORF43 gene or EHV-1 ORF54 gene. In one embodiment, the terminator is BGH. In one embodiment, the linker is a 2A gene. In one embodiment, the expression cassette comprises or consists of a CMV-P1-2A-3C-2A-ORF43-BGH construct. In one embodiment, the expression cassette comprises or consists of a CMV-P1-2A-3C-2A-ORF54-BGH construct. In one embodiment, the nucleotide sequence of CMV-P1-2A-3C-2A-ORF43-BGH construct comprises or is shown by SEQ ID NO: 8. In one embodiment, the nucleotide sequence of CMV-P1-2A-3C-2A-ORF54-BGH construct comprises or is shown by SEQ ID NO: 9.

The present invention further concerns a host cell, comprising the recombinant virus of the present invention. The host cell of the present invention comprises an eukaryotic host cell line, characterized in that it is permissive to replication of the recombinant virus according to the present invention. In one embodiment, said host cell line is a mammalian cell line or an insect cell line, most preferably it is a RK13 cell line, a MDBK cell line, a ST cell line, an AI-ST cell line, a VERO cell line, a Sf9 cell line, a Sf21, a MDCK cell line, and/or derivatives thereof. In one embodiment, the host cell line is a MDBK cell line.

The present invention further concerns a method of preparing a host cell, characterized by the following steps: a). infecting the eukaryotic host cell line with the recombinant virus of the present invention; b). cultivating the infected cells under suitable conditions, and c). optionally harvesting said host cell.

The mammalian host cell lines as listed above are generally cultivated in plastic tissue culture vessels submerged in medium for mammalian cell culture such as Minimal Essential Medium (MEM) supplemented with Earle's salts and fetal bovine serum. The mammalian cell lines are kept in an incubator at 37° C. in regular atmosphere supplemented with 5% CO2 and approximately 80% humidity. The insect cell lines are cultivated in plastic tissue culture vessels submerged in insect cell culture medium and are kept at 27° C. in regular atmosphere in an incubator.

The present invention further concerns an immunogenic composition, a pharmaceutical composition, or vaccine composition, comprising the recombinant virus of the present invention and/or the polypeptide of interest expressed by the recombinant virus of the present invention. In one embodiment, the immunogenic/pharmaceutical/vaccine composition comprises: a). the recombinant virus of the present invention; and/or b). the polypeptide of interest expressed by the recombinant virus of the present invention; and c). optionally a pharmaceutical- or veterinary-acceptable carrier or excipient, preferably said carrier is suitable for oral, intradermal, intramuscular or intranasal application.

The present invention further concerns a method for producing an immunogenic/pharmaceutical/vaccine composition, comprising the following steps: a). infecting the host cell line of the present invention with the recombinant virus of the present invention; b). cultivating the infected cells under suitable conditions; c). harvesting infected cells; d). optionally purifying the harvest of step c); and e). admixing said harvest with a pharmaceutically acceptable carrier. In one embodiment, the harvest is the recombinant virus produced by the infected cells, or the harvest is the polypeptide of interest expressed by the recombinant virus.

The present invention further concerns use of the recombinant virus of the present invention in preparation of an immunogenic/pharmaceutical/vaccine composition. In one embodiment, the immunogenic/pharmaceutical/vaccine composition is used for preventing and/or treating the clinical signs or disease caused by an infection with a pathogen in an animal or for use in a method of treating or preventing an infection with a pathogen in an animal, preferably said animal is a food producing animal such as swine.

The present invention further concerns the recombinant virus of the present invention or the immunogenic/pharmaceutical/vaccine composition of the present invention for use in a method of reducing or preventing the clinical signs or disease caused by an infection with a pathogen in an animal or for use in a method of treating or preventing an infection with a pathogen in an animal, preferably said animal is a food producing animal such as swine.

The present invention further concerns a method for immunizing an animal such as a food producing animal including swine comprising administering to such animal the recombinant virus of the present invention or the immunogenic/pharmaceutical/vaccine composition of the present invention.

The present invention further concerns a method of immunizing an animal such as a food producing animal including swine against a clinical disease caused by a pathogen in said animal, said method comprising the step of administering to the animal the recombinant virus of the present invention or the immunogenic/pharmaceutical/vaccine composition of the present invention, whereby said recombinant virus or said immunogenic/pharmaceutical/vaccine fails to cause clinical signs of infection but is capable of inducing an immune response that immunizes the animal against pathogenic forms of said pathogen.

In one embodiment, immunization results in lessening of the incidence of the particular virus infection in a herd or in the reduction in the severity of clinical signs caused by or associated with the particular virus infection.

Further, the immunization of a food producing animal in need with the immunogenic compositions as provided herewith, results in preventing infection of a food producing animal by virus infection. Even more preferably, immunization results in an effective, long-lasting, immunological-response against said virus infection. It will be understood that the said period of time will last more than 2 months, preferably more than 3 months, more preferably more than 4 months, more preferably more than 5 months, more preferably more than 6 months. It is to be understood that immunization may not be effective in all animals/subjects immunized. However, the term requires that a significant portion of animals/subjects of a herd are effectively immunized.

The present invention further concerns a method for the treatment or prophylaxis of clinical signs caused by a virus in an animal such as a food producing animal of need, the method comprising administering to the animal a therapeutically effective amount of the recombinant virus of the present invention or the immunogenic/pharmaceutical/vaccine composition of the present invention.

Preferably, the clinical signs are reduced by at least 50%, even more preferably by at least 60%, still more preferably by at least 70%, even more preferably by at least 80%, even more preferably by at least 90%, still more preferably by at least 95% most preferably by 100% in comparison to an animal that is not treated or prevented (not immunized) but subsequently infected by the virus.

In one embodiment, the clinical signs or disease as mentioned above is caused by virus of Aphthovirus genus and Alphaherpesvirinae genus, preferably caused by FMDV.

The present invention further concerns a kit for vaccinating an animal, preferably a food producing animal such as swine or cattle, against a disease associated with and/or reducing the incidence or the severity of one or more clinical signs associated with or caused by a pathogen in an animal.

The kit of the present invention comprises: a). dispenser capable of administering a vaccine to said animal; b). the immunogenic/pharmaceutical/vaccine composition of the present invention, and c). optionally an instruction leaflet.

General Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

Molecular Biology Definitions

The term "nucleic acid", "nucleic acid sequence", "nucleotide sequence", "polynucleotide", "polynucleotide sequence", "RNA sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also may include nucleic acids composed of bases other than the five biologically occurring bases (adenine, guanine, thymine, cytosine and uracil).

The term "polypeptides" are biologically occurring short chains of amino acid monomers linked by peptide (amide) bonds. In the context of the present invention, unless indicated, the terms "polypeptides" and "proteins" are interchangeable.

The term "polypeptide of interest" refers to a polypeptide encoded by a polynucleotide sequence of any length that encodes a product of interest. In a specific aspect, the polynucleotide sequence encoding the polypeptide of interest is exogenous. By definition, every polynucleotide sequence or every gene contained in the recombinant virus and the respective protein or RNA encoded thereby is referred to as "exogenous", "exogenous sequence", "exogenous gene", "exogenous coding sequence" or "transgene", especially when it comes from a different (virus) species. In a specific aspect, the polypeptide of interest is an antigenic polypeptide or a therapeutic polypeptide. In a specific aspect, the polypeptide of interest is an FMDV antigen. In the context of the present invention, unless indicated, the terms "polypeptide of interest" and "target protein" are interchangeable.

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. In a specific aspect, a vector may be used for various purposes such as mere transmission of genetic material, for the transfection of host cells or organisms, for expressing of a target gene, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be or be analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 382,425, PCT publications WO 94/16716, WO 96/39491, WO 95/30018; Paoletti, "Applications of pox virus vectors to vaccination: An update," PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051 (recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 406; EPA0 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 3068-3075, 1991; U.S. Pat. Nos. 5,591,439, 5,552,143; WO 98/00166; allowed U.S. application Ser. Nos. 08/675,556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589,466, and as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell is capable of resulting in a specific biological activity, e.g. the expression of a foreign target gene carried by the vector. A viral vector may or may not be replication competent in the target cell, tissue, or organism. A viral vector can incorporate sequences from the genome of any known organism. The sequences can be incorporated in their native form or can be modified in any way to obtain a desired activity. For example, the sequences can comprise insertions, deletions or substitutions. A viral vector can also incorporate an insertion site for an exogenous polynucleotide sequence. In a specific aspect, the viral vector is herpesviridae, for example EHV-1.

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

The term "recombinant virus" is used to describe a virus comprising an exogenous sequence in its genome by artificial manipulation of the viral genome, i.e. a recombinant DNA technology. In a specific aspect, a virus comprising an exogenous sequence such as an exogenous antigen encoding sequence is a recombinant virus. In a specific aspect, the recombinant virus can be regarded as a virus containing an exogenous polynucleotide sequence encoding a polypeptide of interest. In a specific aspect, the recombinant virus is derived from herpesviridae, for example EHV-1, and comprises a target gene.

Recombinant DNA techniques for preparing recombinant virus are well known to those of skill in the art and usually employ construction of a full-length complementary DNA copies (infectious clones) of the viral genome which may then be modified by DNA recombination and manipulation methods.

The term "functionally linked" or "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" or "functionally linked to" the regulatory elements, meaning that the gene or coding region is controlled or influenced by the regulatory element. For instance, a promoter is operably linked to a coding sequence if the promoter effects transcription or expression of the coding sequence.

Furthermore, within the context of the present description the terms "functional linking", "functionally linked", "operably linked" or "operably linked" means that two or more nucleic acid sequences are positioned in a way that permits each of them to be expressed in correct form and function in the desired manner. For example, a polynucleotide is functionally linked to an essential gene sequence if the transcription or translation of the essential gene sequence depends on the correct expression of the polynucleotide.

"Open reading frame" or "ORF" refers to a length of nucleic acid sequence, either DNA or RNA, that comprises a translation start signal or initiation codon, such as an ATG or AUG, and a termination codon and can be potentially translated into a polypeptide sequence.

"Two polynucleotides are within the same ORF" refers to means that two polynucleotides are within the same transcription molecule and share the same translation start signal or initiation codon and the same termination codon. In a specific aspect, the target gene and the essential gene are within the same transcription molecule and share the same translation start signal or initiation codon and the same termination codon.

The term "expression" as used herein refers to transcription and/or translation of a nucleic acid sequence. According to specific aspects of the present invention the term "expression" refers to transcription and/or translation of an exogenous nucleic acid sequence.

The term "expression cassette" or "transcription unit" defines a region within the genome of a recombinant virus that contains one or more genes to be transcribed. In a specific aspect, the genes contained in the expression cassette may be a target gene and an endogenous essential gene of a recombinant virus. In a specific aspect, the genes contained in the expression cassette may be a target gene and an exogenous essential gene. The nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit.

The term "essential gene" means that those genes indispensable for the replication of an organism, and therefore are considered a foundation of life. The term "functional fragment" or a "functional derivative" of an essential gene means that the fragment or derivative still effects essential gene activity. As for a virus, a gene is also considered essential (i.e. has a role in cell culture) if its deletion results in a decrease in virus titre of greater than 10-fold in either a single or multiple step growth curve. Most of essential genes encode proteins to maintain a central metabolism, replicate DNA, translate genes into proteins, maintain a basic cellular structure, and mediate transport processes into and out of the cell. As for a virus, all genes involved in wrapped virion production, actin tail formation, and extracellular virion release were also considered as essential. Two main strategies have been employed to identify essential genes on a genome-wide basis: directed deletion of genes and random mutagenesis using transposons. In the first case, individual genes (or ORFs) are completely deleted from the genome in a systematic way. In transposon-mediated mutagenesis, transposons are randomly inserted in as many positions in a genome as possible, aiming to inactivate the targeted genes. Insertion mutants that are still able to survive or grow are not in essential genes. (Zhang, R., 2009 & Gerdes, S., 2006).

The term "endogenous" as used herein, refers to a polynucleotide or a protein that occurs naturally in the species. An essential gene is said to be "an endogenous essential gene of a virus", meaning that the essential gene occurs naturally in the genome of the virus. In a specific aspect, the target gene is inserted upstream of and functionally linked to the endogenous essential gene of the recombinant virus.

The term "exogenous" as used herein, refers to a polynucleotide or a protein originates or is produced from a foreign species, or if from the same species, is engineered from its original form. In a specific aspect, an endogenous essential gene of the recombinant virus is silenced, and a same exogenous essential gene is inserted downstream of and functionally linked to the target gene.

The term "construct" as used herein, refers to a recombinant nucleic acid such as a plasmid that has been artificially generated.

The terms "regulatory element", "regulatory nucleic acid" "expression control element" are used interchangeably and refer to nucleic acid molecules that can influence the expression of an operably linked coding sequence in a particular host organism. These terms are used broadly to and cover all elements that promote or regulate transcription, including promoters, promoter sequences, core elements required for basic interaction of RNA polymerase and transcription factors, upstream elements, enhancers, and response elements. Exemplary regulatory elements in prokaryotes include promoters, operator sequences and ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry sites (IRES), picornaviridal 2A sequences, and the like, that provide for and/or regulate expression of a coding sequence and/or production of an encoded polypeptide in a host cell.

As used herein, the term "promoter" or "promoter sequence" means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example CMV-5. SV40 large T, HCMV and MCMV immediate early gene 1, human elongation factor alpha promoter.

The term "enhancer" denotes a polynucleotide sequence which in the cis location acts on the activity of a promoter and thus stimulates the transcription of a gene or coding sequence functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3' end of the eukaryotic mRNA and post-transcriptional incorporation of a sequence of about 100-200 adenine nucleotides (polyA tail) at the cleaved 3' end, and thus causes RNA polymerase to terminate transcription. The polyadenylation signal comprises the sequence AATAAA about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

The term "out of frame mutation", also called a framing error or a reading frame shift, refers to a genetic mutation caused by indels (insertions or deletions) of a number of nucleotides in a DNA sequence that is not divisible by three. The out of frame mutation within an ORF will result in abnormal expressions of the genes within the ORF.

The term "gene silencing" is the process of "turning off" a gene, thereby preventing it from expressing in the form of protein production or other forms of expression. Gene silencing is an important laboratory technique, as disabling a gene is a highly effective way of determining the purpose of that gene. A gene may be silenced in a variety of different ways and through one of many different mechanisms. Gene silencing is often considered the same as gene knockout. That is, when genes are knocked out, they are completely erased from the organism's genome and, thus, have no expression. Within the context of the present invention, gene silencing also comprises the reduction of the expression of a gene to such a level that the rest activity of the gene is not sufficient to achieve its function. For example, in a specific aspect, the endogenous essential gene of the virus has been silenced to such a level that the rest activity of the essential gene cannot affect the control of the target gene on the essential gene that is exogenously introduced and is functionally linked to the target gene.

"Host cell" refers to cells where the recombinant virus can replicate. In a specific aspect, the host cell can be an eukaryotic host cell line, preferably a mammalian cell line or an insect cell line.

The host cell comprises not but limited to a RK13 cell line, a MDBK cell line, a ST cell line, an AI-ST cell line, a VERO cell line, a Sf9 cell line, a Sf21, a MDCK cell line, and/or derivatives thereof.

The term "stable expression" or "expression stability", as used herein, means that the recombinant virus is capable of correctly expressing an exogenous polynucleotide during its passage without loss of the exogenous polynucleotide or any out-of-frame mutations in the exogenous polynucleotide. In the context of the present invention, the stable expression of the exogenous polynucleotide is achieved by allowing the exogenous polynucleotide to be functionally linked to an essential gene of the recombinant virus and located upstream of the essential gene. The recombinant virus with loss of the exogenous polynucleotide or any out-of-frame mutations in the exogenous polynucleotide will not replicate and thus will be eliminated from the recombinant virus culture liquid. Thus, the dominant recombinant viruses present in the culture liquid will be those capable of correctly co-expressing the exogenous polynucleotide and the essential gene.

The expression of the exogenous polynucleotide can be determined by various methods, e.g. by ELISA, by Western blotting, by radioimmunoassays, by immunoprecipitation, by assaying for the biological activity of the protein, or by immunostaining of the protein followed by FACS analysis. In a specific aspect, the expression of the exogenous polynucleotide is determined by Western blotting.

EHV-1 Definitions

A "Herpes virus" or "Herpes virus vector" refers to a species in the family Herpesviridae in the order Herpesvirales.

The term "Equid herpes virus vector" or "Equid herpes virus" or "EHV" means a member of the family Herpesviridae affecting horses. To date eight different species of equid herpesviruses have been identified, five belonging to the subfamily Alphaherpesvirinae (EHV-1, EHV-3, EHV-4, EHV-8 and EHV-9) and three to the Gammaherpesvirinae. (http://www.ictvonline.org/virustaxonomy.asp Virus Taxonomy: 2015 Release EC 47, London, UK, July 2015; Email ratification 2016 (MSL #30).

The term "equid" or "equine" or "equin" means of or belonging to the family Equidae, which includes the horses, asses, and zebras, preferably horses. In addition, the term "equid" or "equine" or "equin" encompasses also hybrids of members of the family Equidae (e.g. mules, hinnies, etc.).

The term "EHV-1" means Equid Alphaherpesvirus 1, a member of the subgenus Varicellovirus in the genus Alphaherpesvirinae in the family Herpesviridae. A non-limiting reference sequence for EHV-1 would be for example the wild-type EHV-1 strain ab4 (Genbank accession number AY665713.1) or the RacH (Hilbert 1996). In a specific aspect, the recombinant virus is derived the families of Herpesviridae such as EHV-1 or EHV-4, preferably EHV-1. EHV-1 ORF43 gene encodes a capsid protein known as VP23, which is a component of intercapsomeric triplex (Elizabeth A. R. Telford, et al, Journal of General Virology, 1998, 79, 1197-1203). In one embodiment, the nucleotide sequence of EHV-1 ORF43 gene is shown by SEQ ID NO:5.

EHV-1 ORF54 gene encodes a protein that is a component of DNA helicase-primase complex (Elizabeth A. R. Telford, et al, Journal of General Virology, 1998, 79, 1197-1203). In one embodiment, the nucleotide sequence of EHV-1 ORF54 gene is shown by SEQ ID NO:6.

FMDV Definitions

A "Foot-and-mouth disease virus" or "FMDV" refers to a species in the Aphthovirus genus of the Picornaviridae family.

The term "P1 protein" or "protein P1" means that a precursor protein that contains the 4 capsid proteins, VP4, VP2, VP3 and VP1. During the maturation process, protein P1 is cleaved by protease 3C into three proteins known as VP0, VP1 and VP3. In the virion, protein VP0 is then cleaved into two proteins, VP4 and VP2. In one embodiment, the nucleotide sequence of P1 gene is shown by SEQ ID NO: 1.

The term "2A peptide" or "peptide 2A" is a self-cleaving peptide and used in several families of viruses, the best known FMDV of the Picornaviridae family, for producing multiple polypeptides. In FMDV, 2A peptide is located at the C-terminal of the P1-2A precursor. In one embodiment, the nucleotide sequence of 2A gene is shown by SEQ ID NO: 2.

The term "protease 3C" or "3C protease" means a protease and endopeptidase enzyme found in the picornavirus, that cleaves peptide bonds of non-terminal sequences. 3C protease is located in the P3 precursor and can process P1 precursor protein into VP0 (precursor of VP4 and VP2), VP3 and VP1. In one embodiment, the nucleotide sequence of 3C gene is shown by SEQ ID NO: 3.

P1-2A-3C cassette means a single ORF containing P1 gene and 3C gene that are linked by a sequence containing 2A peptide gene. In one embodiment, the nucleotide sequence of the P1-2A-3C gene cassette is shown by SEQ ID NO: 4.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

The term "food producing animals" mean animals which are used for human consumption such as swine, cattle, poultry and the like, preferably food producing animals mean swine and cattle, most preferably swine. In a specific aspect of the present invention, the "food producing animals" are cloven-hoofed animals, including cattle, sheep, goats and swine, preferably swine.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, New Jersey. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta GA), SAF-M (Chiron, Emeryville CA), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

An adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylenediaminetetraacetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Formulations

The subject to which the composition is administered is preferably an animal, including but not limited to cattle, horses, sheep, pigs, poultry (e.g. chickens), goats, cats, dogs, hamsters, mice and rats, most preferably the mammal is a swine.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Methods of Treatment

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitoneally, intracutaneously, and depending on the desired duration and effectiveness of the treatment, the compositions according to the invention may be administered once or several times, also intermittently, for instance on a daily basis for several days, weeks or months and in different dosages such as about $10^3$ to $10^8$ TCID50 (see viral titre above).

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

Sequences Overview

The following sequences are detailed and disclosed hereby in the present invention:
SEQ ID NO: 1 Nucleotide sequence of P1 gene,
SEQ ID NO: 2 Nucleotide sequence of 2A gene,
SEQ ID NO: 3 Nucleotide sequence of 3C gene,
SEQ ID NO: 4 Nucleotide sequence of the P1-2A-3C gene expression cassette,
SEQ ID NO: 5 Nucleotide sequence of EHV-1 ORF43 gene,
SEQ ID NO: 6 Nucleotide sequence of EHV-1 ORF54 gene,
SEQ ID NO: 7 Nucleotide sequence of BGH poly A signal,
SEQ ID NO: 8 Nucleotide sequence of CMV5-P12A3C2AORF43-BGH cassette,
SEQ ID NO: 9 Nucleotide sequence of CMV5-P12A3C2AORF54-BGH cassette,
SEQ ID NO: 10 Primer sequence, and
SEQ ID NO: 11 Primer sequence.
SEQ ID NO: 12 partial P1 gene sequence showing one nucleotide deletion,
SEQ ID NO: 13 partial P1 gene sequence without deletion,
SEQ ID NO: 14 partial P1 gene sequence without deletion, and
SEQ ID NO: 15 partial P1 gene sequence without deletion.

CLAUSES

The following clauses are described herein:
The present invention provides the following clauses:
1. A recombinant virus comprising an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or functional fragment thereof that is active in the recombinant virus.

2. The recombinant virus of clause 1, wherein the first polynucleotide and the second polynucleotide are within the same ORF.

3. The recombinant virus of clause 1 or 2, wherein the second polynucleotide is an endogenous essential gene of the recombinant.

4. The recombinant virus of clause 1 or 2, wherein the second polynucleotide is exogenous, and the endogenous essential gene of the recombinant virus has been silenced.

5. The recombinant virus of any one of clauses 1-4, wherein the first polynucleotide encodes an antigenic polypeptide or a therapeutic polypeptide.

6. The recombinant virus of clause 5, wherein the antigenic polypeptide is selected from the group consisting of an FMDV antigen, a PRRSV antigen, a DEV antigen, and a PRV antigen, preferably an FMDV antigen.

7. The recombinant virus of any one of clauses 1-4, wherein the first polynucleotide comprises the P1 gene, 2A gene and 3C gene of FMDV.

8. The recombinant virus of any one of clauses 1-7, wherein the recombinant virus is derived from the virus selected from the group consisting of herpesviridae such as Equid Alphaherpesvirus 1 (EHV-1), Equid Alphaherpesvirus 4 (EHV-4) and other Varicelloviruses like Pseudorabies virus (PrV) and Bovine Herpesvirus 1 (BHV-1), Adenoviridae (AdV) such as Canine Adenovirus (CAdV), Adeno-associated viridae, Lentiviridae such as Retroviruses, and Poxviridae.

9. The recombinant virus of clause 8, wherein the virus is a member of the family Herpesviridae, preferably of the genus Alphaherpesvirinae, more preferably of the subgenus Varicellovirus, most preferable of Equid Alphaherpesvirus 1 (EHV-1).

10. The recombinant virus of clause 1, wherein the recombinant virus is derived from EHV-1, and the first polynucleotide comprises the P1 gene, 2A gene and 3C gene of FMDV.

11. The recombinant virus of any one of clauses 1-10, wherein the essential gene encodes a protein selected from the group consisting of a capsid protein, a DNA replication related protein, a DNA helicase, a DNA replicase, a receptor binding protein, and an Egress-related protein.

12. The recombinant virus of clause 11, wherein the recombinant virus is derived from EHV-1, the first polynucleotide comprises the P1 gene, 2A gene and 3C gene of FMDV, and the essential gene is EHV-1 ORF43 gene or EHV-1 ORF54 gene.

13. The recombinant virus of any one of clauses 1-12, wherein the first polynucleotide is linked to the second polynucleotide via a linker.

14. The recombinant virus of clause 13, wherein the linker can be a flexible linker or a 2A gene, preferably a 2A gene.

15. The recombinant virus of any one of clauses 1-13, wherein the first polynucleotide is directly linked to the second polynucleotide.

16. The recombinant virus of any one of clauses 1-15, wherein the expression cassette further comprises regulatory elements, such as a promoter, preferably a CMV5 promoter.

17. The recombinant virus of any one of clauses 1-16, wherein the expression cassette comprises a P1-2A-3C-2A-ORF43 construct or a P1-2A-3C-2A-ORF54 construct, preferably a CMV-P1-2A-3C-2A-ORF43-BGH construct or a CMV-P1-2A-3C-2A-ORF54-BGH construct, more preferably a CMV-P1-2A-3C-2A-ORF43-BGH construct as shown in SEQ ID NO: 8 or a CMV-P1-2A-3C-2A-ORF54-BGH construct as shown in SEQ ID NO: 9.

18. A method for preparing a recombinant virus of any one of clauses 1-17, comprising constructing an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or functional fragment thereof that is active in the recombinant virus.

19. A method for increasing the expression stability of a polypeptide of interest within a recombinant virus, comprising constructing an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or functional fragment thereof that is active in the recombinant virus.

20. The method of clause 19, wherein the first polynucleotide and the second polynucleotide are within the same ORF.

21. The method of clause 19 or 20, wherein the second polynucleotide is the essential gene naturally occurring the genome of the recombinant virus.

22. The method of clause 19 or 20, wherein the second polynucleotide is exogenous, and the essential gene naturally occurring in the genome of the recombinant virus has been silenced.

23. The method of any one of clauses 19-22, wherein the first polynucleotide encodes an antigenic polypeptide or a therapeutic polypeptide.

24. The method of clause 23, wherein the antigenic polypeptide is selected from the group consisting of an FMDV antigen, a PRRSV antigen, a DEV antigen, and a PRV antigen, preferably an FMDV antigen.

25. The method of any one of clauses 19-22, wherein the first polynucleotide comprises the P1 gene, 2A gene and 3C gene of FMDV.

26. The method of any one of clauses 19-22, wherein the recombinant virus is derived from the virus selected from the group consisting of herpes viridae such as Equid Alphaherpesvirus 1 (EHV-1), Equid Alphaherpesvirus 4 (EHV-4) and other Varicelloviruses like Pseudorabies virus (PrV) and Bovine Herpesvirus 1 (BHV-1), Adenoviridae (AdV) such as Canine Adenovirus (CAdV), Adeno-associated viridae, Lentiviridae such as Retroviruses, and Poxviridae.

27. The method of clause 26, wherein the virus is a member of the family Herpesviridae, preferably of the genus Alphaherpesvirinae, more preferably of the subgenus Varicellovirus, most preferable of Equid Alphaherpesvirus 1 (EHV-1).

28. The method of clause 19, wherein the recombinant virus is derived from EHV-1, and the first polynucleotide comprises the P1 gene, 2A gene and 3C gene of FMDV.

29. The method of any one of clauses 19-28, wherein the essential gene encodes a protein selected from the group consisting of a capsid protein, a DNA replication related protein, a DNA helicase, a DNA replicase, a receptor binding protein, and an Egress-related protein.

30. The method of clause 29, wherein the recombinant virus is derived from EHV-1, the first polynucleotide comprises the P1 gene, 2A gene and 3C gene of FMDV, and the essential gene is EHV-1 ORF43 gene or EHV-1 ORF54 gene.

31. The method of any one of clauses 19-30, wherein the first polynucleotide is linked to the second polynucleotide via a linker.

32. The method of clause 31, wherein the linker can be a flexible linker or a 2A gene, preferably a 2A gene.

33. The method of any one of clauses 19-30, wherein the first polynucleotide is directly linked to the second polynucleotide.

34. The method of any one of clauses 19-30, wherein the expression cassette further comprises regulatory elements, such as a promoter, a polyA, etc., preferably a promoter, more preferably a CMV5 promoter.

35. The method of any one of clauses 19-31, wherein the expression cassette comprises a P1-2A-3C-2A-ORF43 construct or a P1-2A-3C-2A-ORF54 construct, preferably a CMV-P1-2A-3C-2A-ORF43-BGH construct or a CMV-P1-2A-3C-2A-ORF54-BGH construct, preferably a CMV-P1-2A-3C-2A-ORF43-BGH construct as shown in SEQ ID NO: 8 or a CMV-P1-2A-3C-2A-ORF54-BGH construct as shown in SEQ ID NO: 9.

36. A host cell comprising the recombinant virus of any one of clauses 1-17, preferably the host cell is an eukaryotic host cell line; more preferably, the host cell line is a mammalian cell line or an insect cell line; most preferably the host cell line is a RK13 cell line, an MDBK cell line, an ST cell line, an AI-ST cell line, a VERO cell line, an Sf9 cell line, an Sf21, an MDCK cell line, and/or derivatives thereof.

37. A method of preparing a host cell of clause 36, characterized by the following steps:
 a. infecting the host cell line with the recombinant virus of any one of clauses 1-17,
 b. cultivating the infected cells under suitable conditions, and
 c. optionally harvesting said host cell.

38. An immunogenic, pharmaceutical, or vaccine composition, comprising:
 a. the recombinant virus of any one of clauses 1-17, and/or
 b. the polypeptide of interest expressed by the recombinant virus of any one of clauses 1-17, and
 b. optionally a pharmaceutical- or veterinary-acceptable carrier or excipient, preferably said carrier is suitable for oral, intradermal, intramuscular or intranasal application 39. A method for the preparation of an immunogenic, pharmaceutical, or vaccine composition, comprising the following steps:
 a. infecting the host cell of clause 36 with the recombinant virus of any one of clauses 1-17,
 b. cultivating the infected cells under suitable conditions,
 c. harvesting infected cells,
 d. optionally purifying the harvest of step c), and
 e. optionally admixing said harvest with a pharmaceutically acceptable carrier.

40. The method of clause 39, wherein the harvest is the recombinant virus produced by the infected cells, or the harvest is the polypeptide of interest expressed by the recombinant virus.

41. Use of the recombinant virus of any one of clauses 1-17 in preparation of an immunogenic, pharmaceutical or vaccine composition for preventing and/or treating the clinical signs or a disease caused by an infection with a pathogen in an animal, or for use in a method of treating or preventing an infection with a pathogen in an animal, preferably said animal is a food producing animal such as swine.

42. The recombinant virus of any one of clauses 1-17 or the immunogenic, pharmaceutical or vaccine composition of clause 38, for use in a method of reducing or preventing the clinical signs or a disease caused by an infection with a pathogen in an animal, or for use in a method of treating or preventing an infection with a pathogen in an animal, preferably said animal is a food producing animal such as swine.

43. A method of immunizing, treating or preventing an animal, such as a food producing animal such as swine or cattle, against a disease caused by a pathogen in said animal, said method comprising the step of administering to the animal the recombinant virus of any one of clauses 1-17 or the immunogenic, pharmaceutical or vaccine composition of clause 38.

44. A kit for vaccinating an animal, preferably a food producing animal such as swine or cattle, against a disease associated with and/or reducing the incidence or the severity of one or more clinical signs associated with or caused by a pathogen in an animal, comprising:
 a. dispenser capable of administering the recombinant virus of any one of clauses 1-17 or the immunogenic, pharmaceutical or vaccine composition of clause 38 to said animal;
 b. the recombinant virus of any one of clauses 1-17 or the immunogenic, pharmaceutical or vaccine composition of clause 38, and
 c. optionally an instruction leaflet.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7. Confirmation of FMDV protein expression and EHV-1 ORF71 restoration by IFA. The recombinant viruses with EHV-1 ORF43 or ORF54 translocation could be rescued after transfection. The expression of FMDV target protein was confirmed by IFA. EHV-1 gp2 was stained to show to the presence of EHV-1 plaques.

FIG. 8. A series of recombinant EHV-1 were constructed with regular design, but cannot express target protein stably. (A) negative EHV-1 plaques were found by dual IFA; (B) sequencing of the negative plaques showed random genetic changes, including single nucleotide acid deletion, resulting in an out of frame mutation of the downstream genes.

FIG. 9. Illustration of a representative dual IFA result, showing the plaques that can express both target FMDV protein and EHV-1 proteins.

FIG. 10. Detection of FMDV VLP from different passage levels of the recombinant viruses.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In the study, unless any exception is noted, all materials are commercially available and were purchased from QIAGEN, Promega, Thermo Fisher and BIO-RAD.

Figure 1:
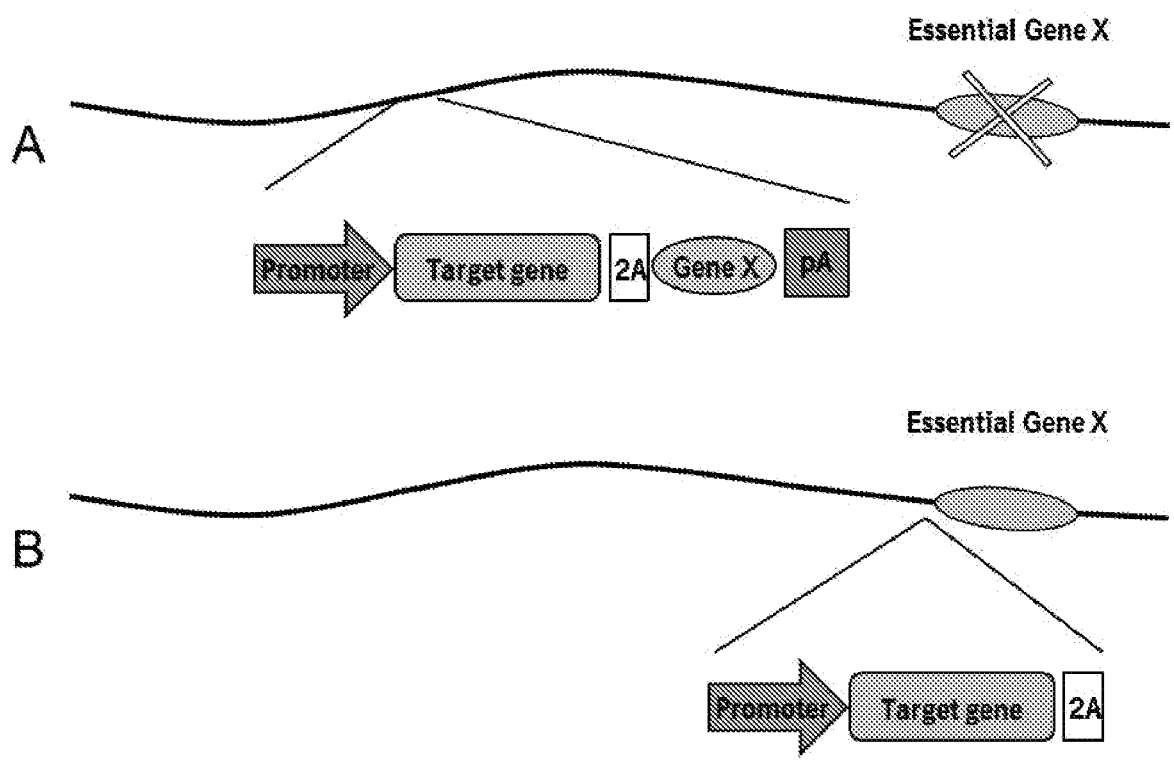
FIG. 1. Illustration of essential gene translocation concept. A: an essential gene was deleted and translocated with target gene; and B: the target gene can also be inserted at the upstream of the essential gene at its original location.
Figure 2:
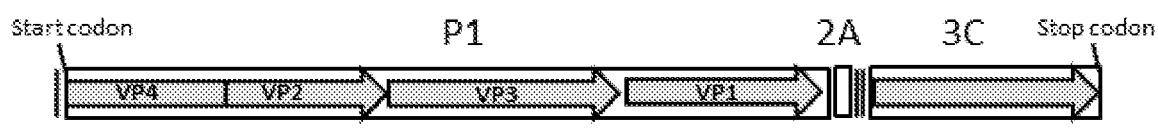
FIG. 2. The design of FMDV P12A3C cassette.

Example 1: Construction of the Recombinant EHV-1 of the Invention which can Stably Express FMDV Antigens 1.1 Construction of FMDV P1-2A-3C Gene Expression Cassette To express FMDV VLP, a gene expression cassette P1-2A-3C, derived from FMDV serotype 0 strain (GenBank ID: JN998085), was designed. In this study, FMDV P1-2A-3C gene expression cassette was chemically synthesized by Genscript based on the nucleotide sequences of P1 gene (SEQ ID NO: 1), 2A gene (SEQ ID NO: 2) and 3C gene (SEQ ID NO: 3). The nucleotide sequence of the synthetic P1-2A-3C gene expression cassette used in the study is shown by SEQ ID NO: 4. The design of P1-2A-3C cassette was illustrated in FIG. 2.

1.2 Construction of Transfer Plasmids

A transfer vector pUC19-CMV5-ORF1/3-linker (Genscript), which contains homologous flanking regions for the two-step Red-mediated recombination, the kanamycin resistant gene as well as promoter and BGH poly A signal, was used in the study.

Figure 3:
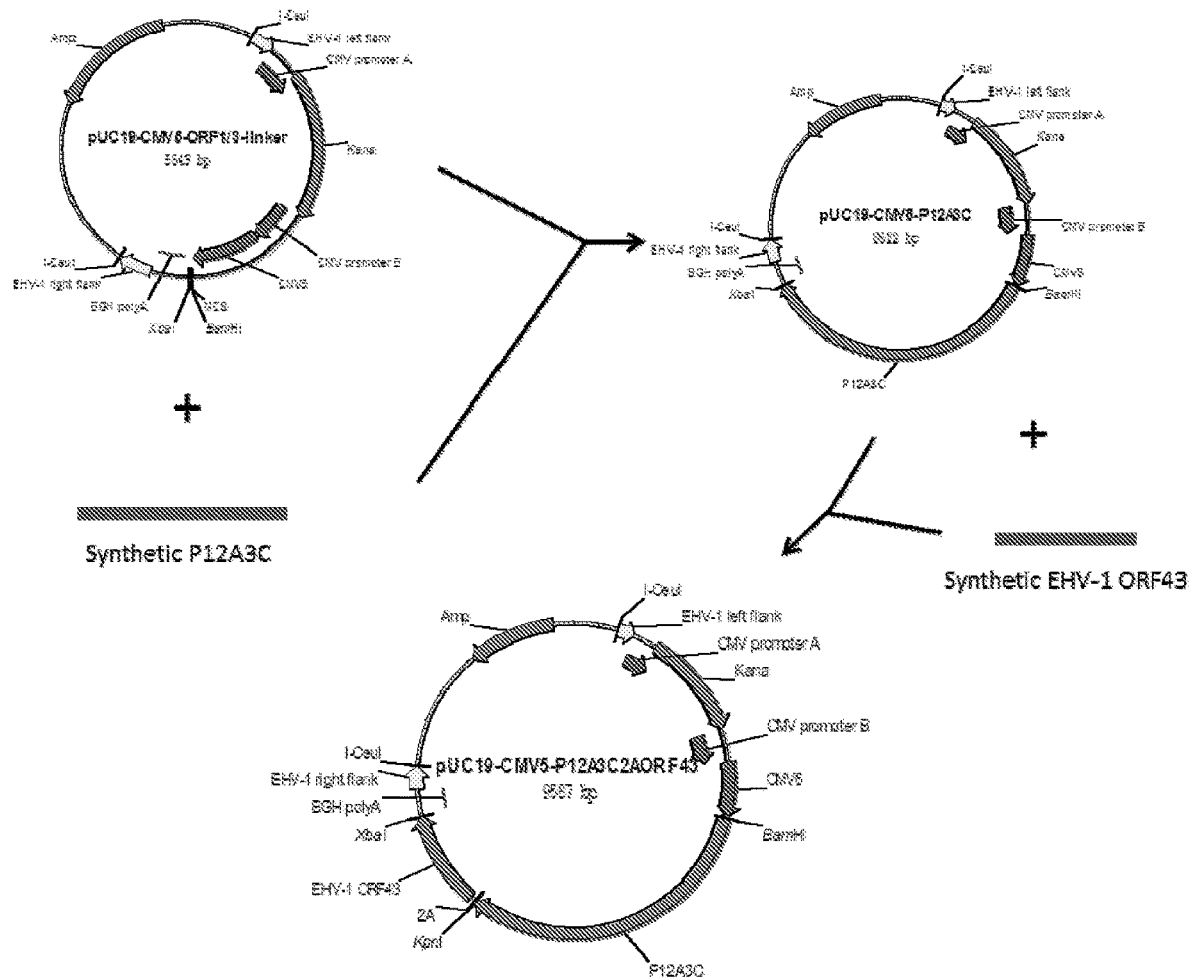
FIG. 3. The construction procedure of the transfer plasmid was illustrated. The target gene P12A3C was synthesized and cloned into vector pUC19-CMV5-ORF1/3-linker, resulting in pUC19-CMV5-P12A3C. EHV-1 essential gene ORF43 or ORF54 was also synthesized and cloned into pUC19-CMV5-P12A3C, resulting in the final transfer plasmid, which was used to generate recombinant EHV-1.

To generate transfer plasmids, P1-2A-3C gene (SEQ ID NO: 4) was inserted into the transfer vector at site of ORF1/3. Then, ORF43 gene (SEQ ID NO:5) and ORF54 gene (SEQ ID NO:6) were chemically synthesized and cloned into the downstream of P1-2A-3C gene (SEQ ID NO: 4), resulting in transfer plasmids pUC19-CMV5-P12A3C2AORF43 and pUC19-CMV5-P12A3C2AORF54, respectively. The construction procedure of the transfer plasmid pUC19-CMV5-P12A3C2AORF43 was illustrated in FIG. 3.

Figure 4:
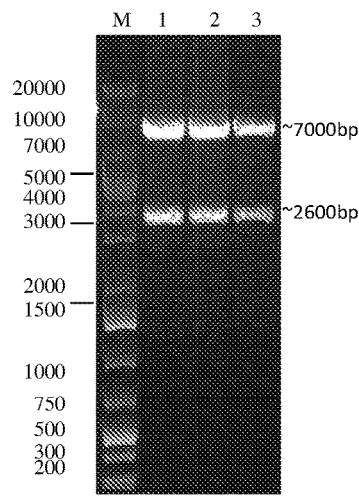
FIG. 4. Gel electrophoresis result of CMV5-P12A3C2AORF43-BGH. Digestion of transfer plasmid with restriction enzyme I-CeuI. After digestion, a target fragment around 7 kb was released and used for recombination.

The transfer plasmids were digested by restriction enzyme I-CeuI (NEB), two fragments around 7 kb containing CMV5-P12A3C2AORF43-BGH (SEQ ID NO. 8) and CMV5-P12A3C2AORF54-BGH (SEQ ID NO. 9) were released respectively, which then were gel purified (Invitrogen) and confirmed via gel electrophoresis. The released fragments were used for further recombination. The gel electrophoresis result of CMV5-P12A3C2AORF43-BGH was illustrated in FIG. 4.

1.3 Construction of EHV-1 Viral Vector

EHV-1 vaccine strain RacH (Patel, J R and Heldens, J, 2005) was used as the viral vector to express serotype 0 FMDV gene P12A3C in this study. RacH strain has lost its virulence in the natural host, namely horse, and has since been used as a modified live vaccine (MLV) in both Europe and the USA (Patel, J R and Heldens, J, 2005). RacH viral genome was constructed as bacterial artificial chromosome (BAC) by replacing the most part of ORF71 gene (encoding for gp2) with mini-F replicon sequence, and the Bacmid was designated as pRacH (Rudolph and Osterrieder, 2002, Virology 293, 2002, 356-367; U.S. Pat. No. 7,482,441B2).

Figure 5:
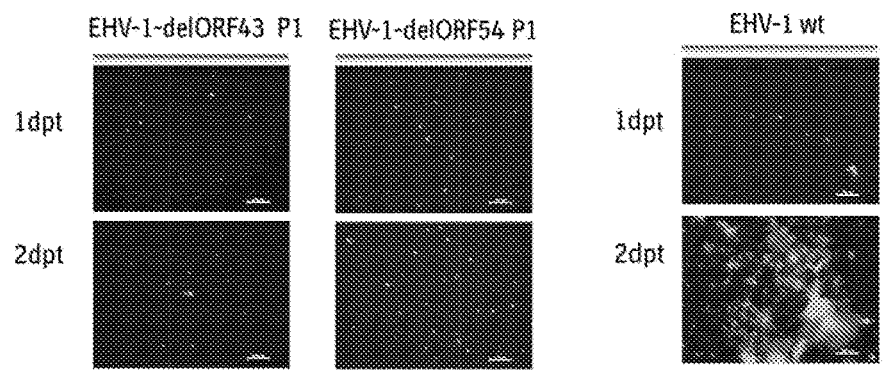
FIG. 5. The gene ORF43 or ORF54 was deleted from EHV-1 vector and the deletion mutant virus was unable to replicate in vitro. As a control, EHV-1 wild type could be easily rescued and propagated well 2 days after transfection. Since the rescued virus contains EGFP gene, the plaques show green fluorescence.

In this study, the essential genes ORF43 gene and ORF54 gene were deleted from pRacH respectively, and the pRacH with deleted ORF43 gene (shown as EHV-1-delORF43 P1 in FIG. 5) and the pRacH with deleted ORF54 gene (shown as EHV-1-delORF54 P1 in FIG. 5) were identified by restriction fragment length polymorphism (RFLP) analysis.

By transfecting the EHV-1-delORF43 P1 and EHV-1-delORF54 P1 into MDBK cells, it was confirmed that the deletion mutants were unable to replicate in cell culture. The results were shown below in FIG. 5.

1.4 Construction of the Recombinant EHV-1 of the Invention

Figure 6:
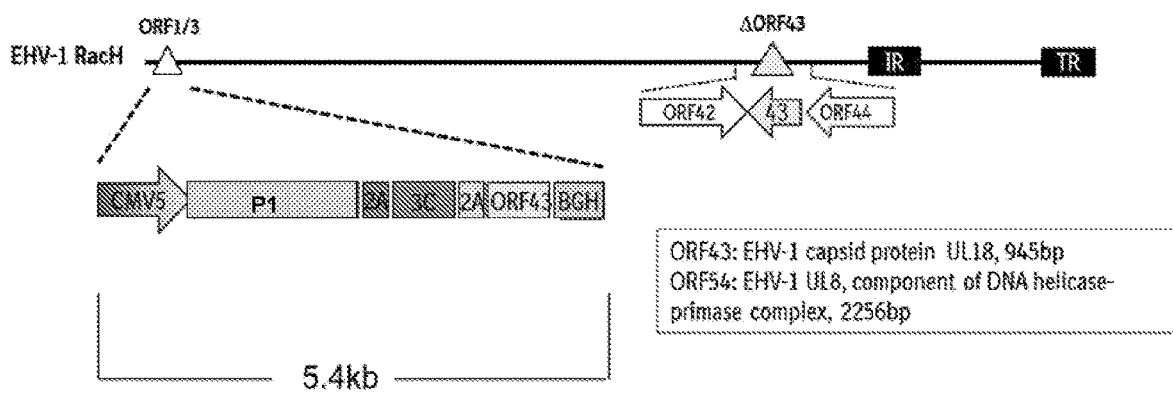
FIG. 6. Gene structure of the recombinant EHV-1 with ORF43 gene translocation. ORF43 gene was deleted from its original position and translocated to the downstream of FMDV P12A3C gene.

The recombinant EHV-1 of the invention was constructed via a two-step Red-mediated recombination strategy (Tischer B K et al, BioTechniques 2006 (40), 191-197). Particularly, the transfer plasmids obtained in the step 1.2 were digested to release the fragments of CMV5-P12A3C2AORF43-BGH (SEQ ID NO. 8) and CMV5-P12A3C2AORF54-BGH (SEQ ID NO. 9) respectively. The two released fragments were electroporated into *E. coli* competent cells containing EHV-1-delORF43 P1 and EHV-1-delORF54 P1, respectively. The gene structure of the recombinant virus was illustrated in FIG. 6. Recombinant clones were then selected on chloramphenicol and kanamycin double resistant LB agar plates. The recombinant Bacmid DNA was extracted and analyzed by both PCR and RFLP methods. In the 2nd step of Red recombination, 1% arabinose was used to induce expression of the homing endonuclease I-SceI, resulting in the cleavage of the I-SceI restriction site upstream of the kanamycin gene and, ultimately, the excision of the kanamycin cassette.

1.5 Virus Rescue and Purification

To rescue the recombinant EHV-1, the recombinant Bacmid DNA was extracted and transfected into MDBK cells (Sigma) in a 6-well plate using lipofectamine 3000 (Thermo Fisher). After transfection, cells were observed daily to check formation of both GFP-positive and -negative plaques. The transfected cells together with the culture supernatant were frozen and thawed twice, cleared by centrifugation and the recombinant virus, defined as passage 1, was stored at −80° C. for later analysis. Limiting dilution or plaque purification was performed to separate the GFP-negative recombinant virus, in which mini-F containing EGFP gene was removed and the missing ORF71 was restored via intra-molecular homologous recombination mechanism. Each round of the limiting dilution was recognized as one passage.

Figures 7, 8:
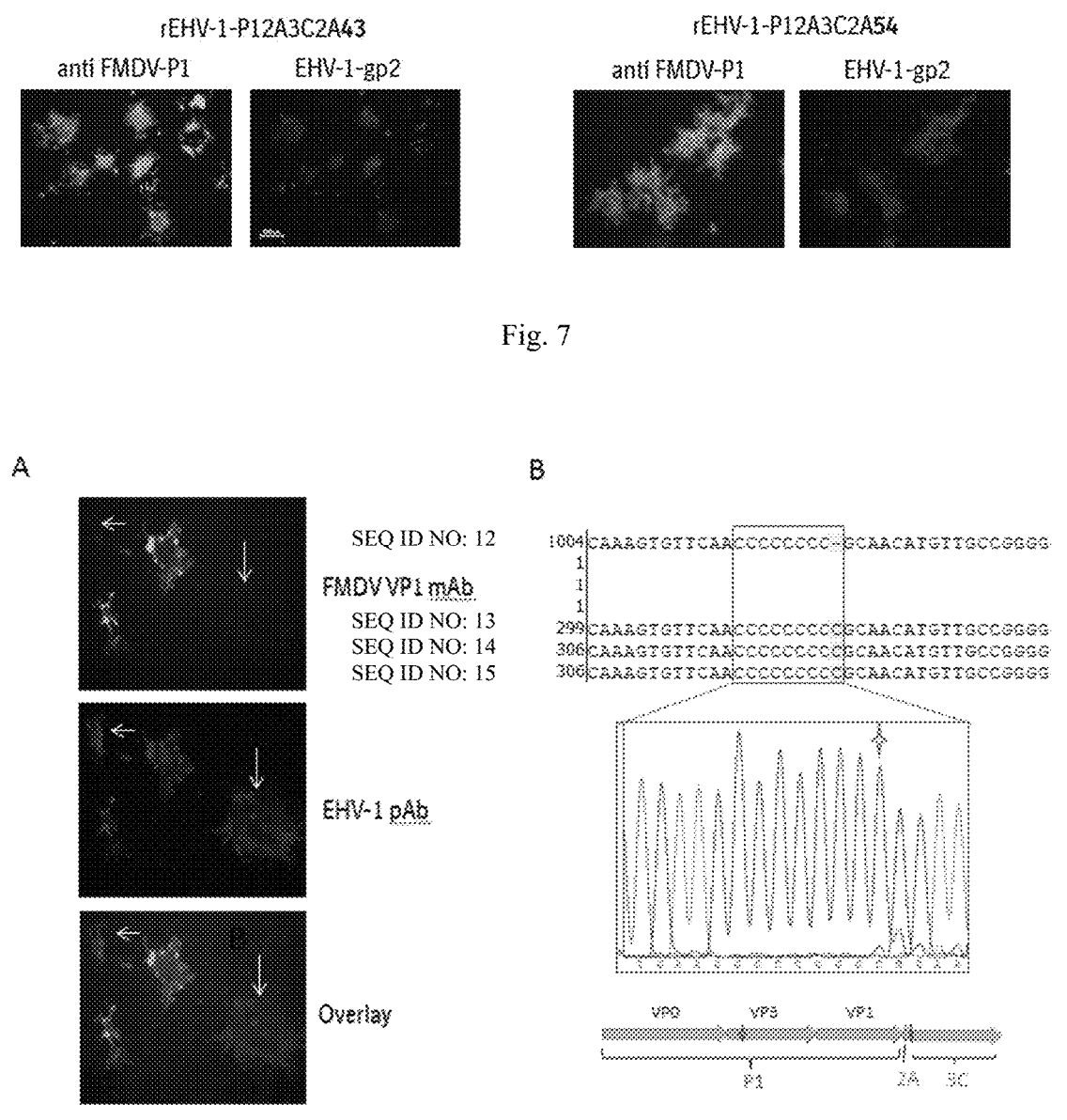

Example 2: Expression and Detection of the FMDV Protein 2.1 IFA, Sucrose Gradient Centrifugation and Western Blot To confirm the expression of FMDV proteins, indirect fluorescence assay (IFA) was performed using monoclonal antibody against FMDV VP1 (Jeno-Biotech, Cat #9172). MDBK cells were infected and overlaid with 1.5% Methyl Cellulose. Three days after infection, cells were washed with 1×PBS, fixed with 4% Formaldehyde, permeated by 0.1% Triton X-100, and stained with the corresponding antibodies. The expression of FMDV protein was confirmed by IFA (FIG. 7).

For western blot analysis, the infected cell pellets were lysed and mixed with 4×LDS sample buffer (Invitrogen) and Nupage 10× reducing reagent (Invitrogen). After heating at 85° C. for the proteins were separated on the NuPAGE gels (Invitrogen) and transferred to PVDF membrane (Lifetech). After membrane blocking, the membrane was incubated with anti-FMDV VP1 mAb (1st antibody, Jeno-Biotech) for 1 h, and then with anti-mouse IgG-HRP (2nd antibody, Santa-Cruz) for 1 h after washing. The image was developed after applying the membrane with Supersignal West Femto Maximum Sensitivity substrate (Thermo Scientific).

To confirm the formation of FMDV VLP, infected cell culture was pre-cleared by centrifugation and concentrated by ultrafiltration using Amicon Ultra-15 mL centrifuge filter (Merk, Ultracel-100 KDa), then applied to 10%-60% sucrose gradient ultracentrifugation at 53,720 g for 22h at 10° C. The sucrose gradient was separated to 14 fractions from up to down. The proteins in each fraction were analyzed by western blot using anti-FMDV VP1 mAb as described above.

Example 3: Study of Stability of the FMDV Protein Expression 3.1 FMDV P1-2A-3C Gene Cannot be Stably Expressed with Regular Design Different recombinant EHV-1 as controls (with different promoters and insertion sites) were constructed with a regular design of directly introducing FMDV P1-2A-3C gene into EHV-1 viral vector. The results of the genetic stability testing of different recombinant EHV-1 are summarized in the table below.

TABLE 1

Summary of genetic stability testing of different recombinant EHV-1

| P1-2A-3C cassette | Promoter | Insertion site | Cell line | Genetic stability |
|---|---|---|---|---|
| SEQ ID NO: 4 | CMV | ORF1/3 | MDBK | unstable after P3 |
| SEQ ID NO: 4 | EHV-4 gG | ORF1/3 | MDBK | unstable after P4 |
| SEQ ID NO: 4 | CMV | ORF70 (gG) | MDBK | unstable after P5 |

It can be seen that, by using regular design, FMDV P1-2A-3C gene cannot be stably maintained and tended to lose target protein expression during continuous passages, as shown by dual IFA (FIG. 8A). Sequencing analysis also showed that there were random deletions in the insert (FIG. 8B).

3.2 Essential Gene Translocation to Solve Genetic Stability Issue

Figures 9, 10:
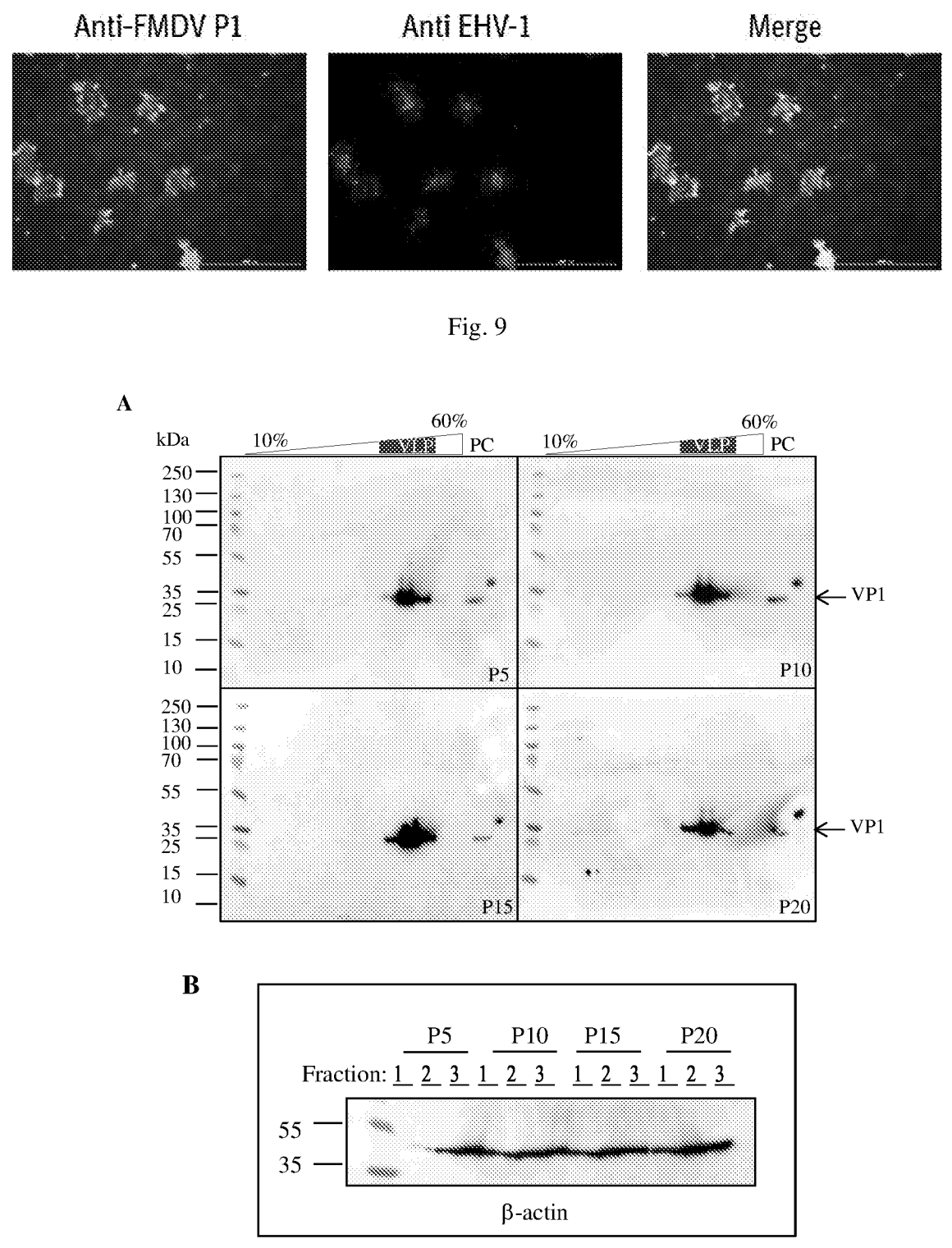

To evaluate whether FMDV protein could be stably expressed by the recombinant EHV-1 of the invention, the recombinant EHV-1 of the invention was continuously passaged on MDBK cells with MOI 0.01. After each passaging, fresh MDBK cell monolayers were infected with the recombinant virus with appropriate dilution and overlaid with 1.5% Methyl Cellulose. Three days post infection, dual IFA was performed using a mixture of anti-FMDV VP1 mAb and Caprine anti-EHV-1 pAb (VMRD). Individual plaques were examined under fluorescence microscopy. Plaques that are stained with both FMDV VP1 and EHV-1 antibodies were recognized as positive, while those only showing EHV-1 staining are negative. The positive plaque rate was calculated and compared between different passage levels. A representative dual IFA results was shown in FIG. 9.

At every 5 passages (P5, P10, P15 and P20), viral DNA was extracted from infected cells and the complete insert was PCR amplified (forward primer: taacaccatggcaggcctgttg (SEQ ID NO:10), reverse primer: gagcgattcgcacctcatctcc (SEQ ID NO:11)) using high fidelity Accuprime pfx DNA polymerase (Invitrogen). The PCR product was then sequenced. In addition, the expression of VLP was detected using sucrose gradient centrifugation and western blot every 5 passages (Rational Engineering of Recombinant Picornavirus Capsids to Produce Safe, Protective Vaccine Antigen. PLOS Pathogens. 2013 March; 9(3):e1003255.). The results of FMDV VLP from different passage levels of the recombinant EHV-1 were shown in FIG. 10.

The percentage of FMDV protein positive plaques out of total EHV-1 plaques was calculated and shown in Table 2. The results showed clearly that FMDV protein can be stably expressed during the passage at least till P20.

TABLE 2

Percentage of FMDV protein positive plaques out of total EHV-1 plaques at each passage

| Passage | Positive rate |
|---|---|
| P5 | 355/355 (100%) |
| P6 | 274/274 (100%) |
| P7 | 155/155 (100%) |
| P8 | 234/234 (100%) |
| P9 | 85/85 (100%) |
| P10 | 173/173 (100%) |
| P11 | 108/108 (100%) |
| P12 | 78/78 (100%) |
| P13 | 175/175 (100%) |
| P14 | 44/44 (100%) |
| P15 | 109/109 (100%) |
| P16 | 202/202 (100%) |
| P17 | 120/120 (100%) |
| P18 | 172/172 (100%) |
| P19 | 295/295 (100%) |
| P20 | 173/173 (100%) |

Figure 11:
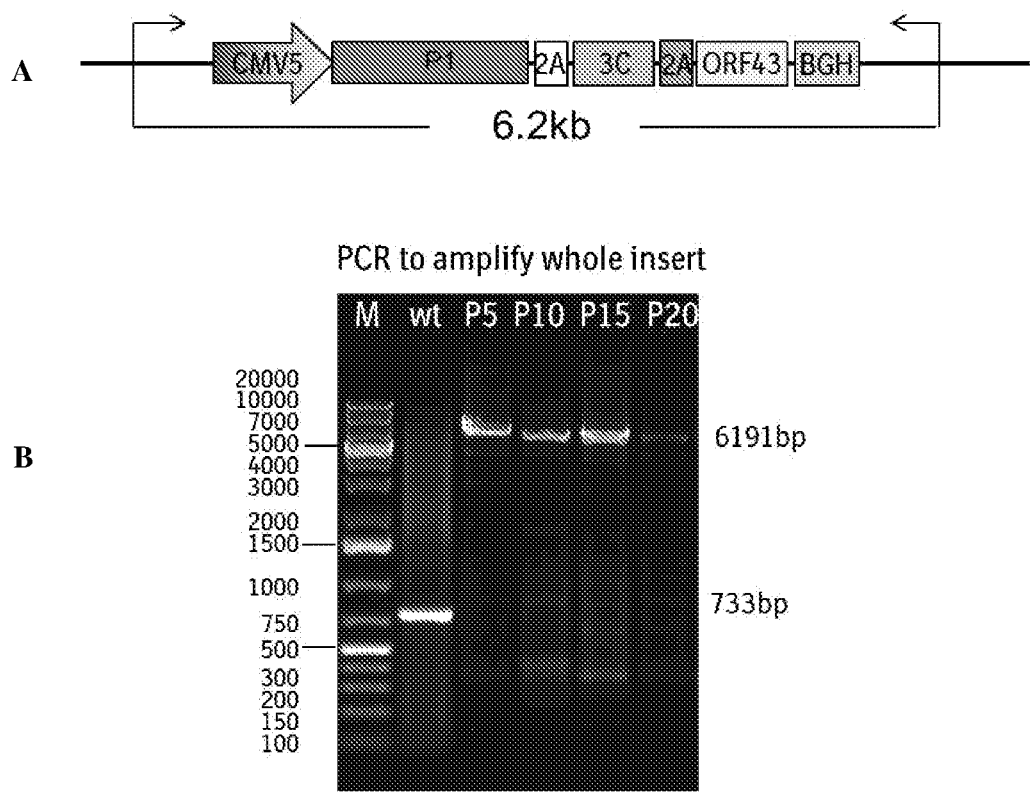
FIG. 11. A: Illustration of the target gene expression cassette and the primer location; B: PCR results from different passage levels of the recombinant viruses.

The viral DNA from each five passages was extracted from the recombinant EHV-1 and PCR was used to amplify the whole insert. The results showed that the whole insert can be amplified with no obvious difference of fragment length (FIG. 11), indicating that no genetic change occurred during continuous virus passage. The PCR product was also sequenced and revealed no genetic changes.

Example 4: In Vitro Growth Kinetics of the Recombinant Viruses

To evaluate the in vitro growth property of the recombinant virus, MDBK cells in 24-well plates were infected by the parental virus and the recombinant virus with MOI of 5. After 2h attachment at 37° C., cells were washed with citrate buffer (pH 3.0). At different time points, culture supernatant was harvested and titrated.

Figure 12:
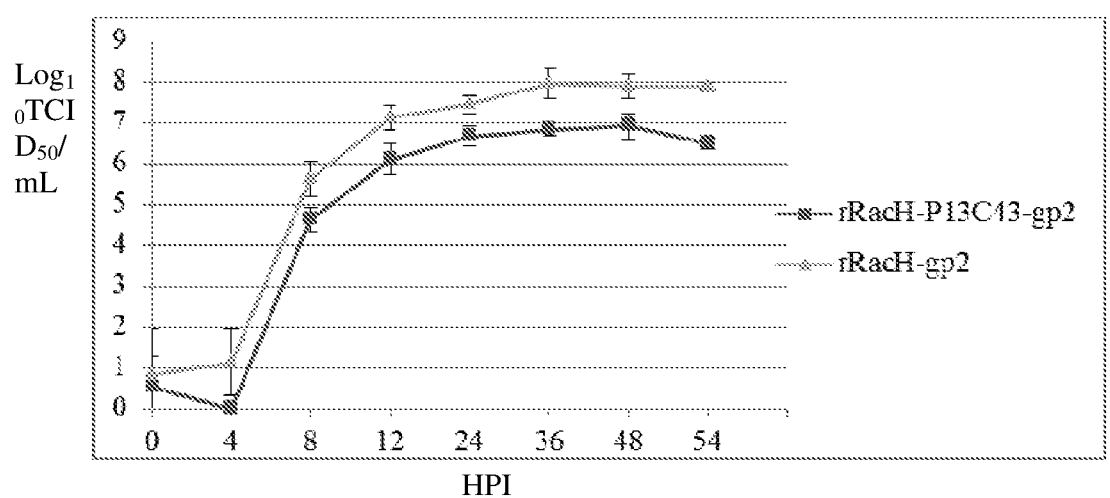
FIG. 12. In vitro single step growth kinetics of recombinant EHV-1 compared with parental EHV-1.

The single step growth kinetics of both recombinant viruses with ORF43 or ORF54 translocation was determined and compared with the parent virus. As can be seen in FIG. 12, the recombinant virus had similar growth kinetics with the parental virus and can reach peak titer at 36h post infection, however, the peak was about 1 log TCID50/mL lower than the parental virus, which was expected, since the expression of the foreign protein will affect the virus growth.

It can be determined from the above experimental data: (1) with regular design, FMDV target protein could not be stably expressed; (2) EHV-1 ORF43 or ORF54 are essential genes for EHV-1 replication; and (3) rEHV-1/FMD constructs of the invention could express target protein with significantly improved stability, while maintaining comparable growth capability to parental EHV-1.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as

The invention claimed is:

1. A recombinant virus comprising an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or functional fragment thereof that is active in the recombinant virus, and wherein the first polynucleotide and the second polynucleotide are within the same open reading frame (ORF).

2. The recombinant virus of claim 1, wherein the second polynucleotide is an endogenous essential gene of the recombinant virus; or
wherein the second polynucleotide is exogenous, and the endogenous essential gene of the recombinant virus has been silenced.

3. The recombinant virus of claim 1, wherein the first polynucleotide encodes an antigenic polypeptide or a therapeutic polypeptide.

4. The recombinant virus of claim 3, wherein the antigenic polypeptide is selected from the group consisting of an FMDV antigen, a PRRSV antigen, a DEV antigen, and a PRV antigen.

5. The recombinant virus of claim 4, wherein the first polynucleotide comprises the P1 gene, 2A gene and 3C gene of FMDV.

6. The recombinant virus of claim 4, wherein the antigenic polypeptide is an FMDV antigen.

7. The recombinant virus of claim 1, wherein the recombinant virus is derived from herpesviridae.

8. The recombinant virus of claim 7, wherein the virus derived from herpesviridae is EHV-1.

9. The recombinant virus of claim 1, wherein the recombinant virus is derived from EHV-1, and the first polynucleotide comprises the P1 gene, 2A gene and 3C gene of FMDV.

10. The recombinant virus of claim 1, wherein the essential gene encodes a protein selected from the group consisting of a capsid protein, a DNA replication related protein, a DNA helicase, a DNA replicase, a receptor binding protein, and an Egress-related protein.

11. The recombinant virus of claim 1, wherein the first polynucleotide is linked to the second polynucleotide via a linker; or wherein the first polynucleotide is directly linked to the second polynucleotide.

12. The recombinant virus of claim 11, wherein the linker can be a flexible linker or a 2A gene.

13. The recombinant virus of claim 12, wherein the linker is a 2A gene.

14. The recombinant virus of claim 1, wherein the expression cassette further comprises regulatory elements.

15. The recombinant virus of claim 14, wherein the regulatory element is a promoter.

16. The recombinant virus of claim 15, wherein the promoter is a CMV5 promoter.

17. A recombinant virus comprising an expression cassette in the genome of the recombinant virus, wherein the expression cassette comprises a first polynucleotide encoding at least one polypeptide of interest, and a second polynucleotide which is an essential gene of the recombinant virus or a functional fragment thereof;
wherein the first polynucleotide is functionally linked to the second polynucleotide with the first polynucleotide being located upstream of the second polynucleotide;
wherein said second polynucleotide is the only copy of said essential gene or functional fragment there that is active in the recombinant virus;
wherein the first polynucleotide and the second polynucleotide are within the same ORF; and
wherein the recombinant virus is derived from EHV-1, the first polynucleotide comprises the P1 gene, 2A gene and 3C gene of FMDV, and the essential gene is EHV-1 ORF43 gene or EHV-1 ORF54 gene.

18. A recombinant virus, comprising an expression cassette in the genome of the recombinant virus, wherein the expression cassette comprises a first polynucleotide encoding at least one polypeptide of interest, and a second polynucleotide which is an essential gene of the recombinant virus or a functional fragment thereof;
wherein the first polynucleotide is functionally linked to the second polynucleotide with the first polynucleotide being located upstream of the second polynucleotide;
wherein said second polynucleotide is the only copy of said essential gene or functional fragment there that is active in the recombinant virus;
wherein the first polynucleotide and the second polynucleotide are within the same ORF;
wherein the expression cassette further comprises regulatory elements; and
wherein the expression cassette comprises a P1-2A-3C-2A-ORF43 construct or a P1-2A-3C-2A-ORF54 construct.

19. A recombinant virus, comprising an expression cassette in the genome of the recombinant virus, wherein the expression cassette comprises a first polynucleotide encoding at least one polypeptide of interest, and a second polynucleotide which is an essential gene of the recombinant virus or a functional fragment thereof;
wherein the first polynucleotide is functionally linked to the second polynucleotide with the first polynucleotide being located upstream of the second polynucleotide;
wherein said second polynucleotide is the only copy of said essential gene or functional fragment there that is active in the recombinant virus;
wherein the first polynucleotide and the second polynucleotide are within the same ORE; and
wherein the expression cassette comprises a CMV-P1-2A-3C-2A-ORF43-BGH construct as shown in SEQ ID NO.: 8, or a CMV-P1-2A-3C-2A-ORF54-BGH construct as shown in SEQ ID NO.: 9.

20. A method for preparing a recombinant virus of claim 1, comprising constructing an expression cassette in the genome of the recombinant virus, wherein the expression cassette comprises a first polynucleotide encoding at least one polypeptide of interest, and a second polynucleotide which is an essential gene of the recombinant virus or a functional fragment thereof, and wherein the first polynucleotide is functionally linked to the second polynucleotide with the first polynucleotide being located upstream of the second polynucleotide, and wherein said second polynucleotide is the only copy of said essential gene or functional fragment thereof that is active in the recombinant virus.

21. An immunogenic, pharmaceutical, or vaccine composition, comprising:
   a. the recombinant virus of claim 1, and/or
   b. the polypeptide of interest expressed by the recombinant virus of claim 1, and
   c. optionally a pharmaceutical- or veterinary-acceptable carrier or excipient.

22. A method of immunizing, treating or preventing an animal, against a disease caused by a pathogen in said animal, said method comprising the step of administering to the animal the recombinant virus of claim 1 or the immunogenic, pharmaceutical or vaccine composition of claim 21.

23. The immunogenic, pharmaceutical, or vaccine composition of claim 21, wherein the carrier is suitable for oral, intradermal, intramuscular, or intranasal application.

24. The method of claim 22, wherein the animal is a food producing animal.

25. The method of claim 24, wherein the food producing animal is swine or cattle.

* * * * *